US008017577B2

(12) United States Patent
Cooper et al.

(10) Patent No.: US 8,017,577 B2
(45) Date of Patent: Sep. 13, 2011

(54) LYOPHILIZABLE AND ENHANCED COMPACTED NUCLEIC ACIDS

(75) Inventors: Mark J. Cooper, Moreland Hills, OH (US); Murali K. Pasumarthy, Twinsburg, OH (US); Tomasz H. Kowalczyk, University Heights, OH (US); Maureen Costello, Beachwood, OH (US)

(73) Assignee: Copernicus Therapeutics, Inc., Cleveland, OH (US)

( * ) Notice: Subject to any disclaimer, the term of this patent is extended or adjusted under 35 U.S.C. 154(b) by 1469 days.

(21) Appl. No.: 10/656,192

(22) Filed: Sep. 8, 2003
(Under 37 CFR 1.47)

(65) Prior Publication Data
US 2004/0048787 A1   Mar. 11, 2004

Related U.S. Application Data

(63) Continuation of application No. 09/867,693, filed on May 31, 2001, now abandoned.

(60) Provisional application No. 60/287,419, filed on May 1, 2001, provisional application No. 60/207,949, filed on May 31, 2000.

(51) Int. Cl.
*A61K 48/00* (2006.01)
(52) U.S. Cl. .............................................. 514/8; 514/44
(58) Field of Classification Search .................. None
See application file for complete search history.

(56) References Cited

U.S. PATENT DOCUMENTS

| 5,656,611 A | 8/1997 | Kabanov et al. |
| 5,844,107 A | 12/1998 | Hanson et al. |
| 6,008,336 A | 12/1999 | Hanson et al. |
| 6,126,964 A * | 10/2000 | Wolff et al. ................ 424/450 |
| 6,177,274 B1 | 1/2001 | Park et al. |
| 6,281,005 B1 | 8/2001 | Casal et al. |
| 6,312,727 B1 | 11/2001 | Schacht et al. |
| 6,506,890 B1 | 1/2003 | Cooper et al. |

FOREIGN PATENT DOCUMENTS

| EP | 1031626 | 8/2000 |
| JP | 09-504174 A | 4/1997 |
| JP | 10-503469 A | 3/1998 |
| WO | 95/11987 A1 | 5/1995 |
| WO | 95/25809 A1 | 9/1995 |
| WO | WO 97/30731 | 8/1997 |
| WO | WO 98/19710 | 5/1998 |
| WO | WO 98/46274 | 10/1998 |
| WO | WO 01/80897 | 11/2001 |

OTHER PUBLICATIONS

Kwoh et al. Stabilization of poly-L-lysine/DNA polyplexes for in vivo gene delivery to the liver. Biochimica et Biophysica Acta 1444 (1999) 171-190.*
Mao et al. Chitosan-DNA nanoparticles as gene carriers: synthesis, characterization and transfection efficiency .Journal of Controlled Release 70 (2001) 399-421.*
Patterson, Amy. Statement of Amy Patterson MD. Subcommittee on Public Health. US Senate. Feb. 2, 2000.*
Orkin et al. NIH Report, Dec. 1995.*
Ferrari et al. (Advanced Drug Delivery Reviews 54 (2002) 1373-1393).*
Konstan et al. (Human Gene Therapy, 2004, 15:1255-1269).*
Martin et al. FEBS Letters. 2000; 480: 106-112.*
Aberle, et al., "The counterion influence on cationic lipid-mediated transfection of plasmid DNA", Biochemica et Biophysica Acta, 1996, pp. 281-283, Elsevier Science B.V.
Allison, et al., "Mechanisms of Protection of Cationic Lipid-DNA Complexes During Lyophilization", Journal of Pharmaceutical Sciences, 2000, pp. 682-691, vol. 89, No. 5, Wiley-Liss, Inc., & American Pharmaceutical Association.
Choi, et al., "Lactose-Poly (ethylene Glycol)-Grafted Poly-$_L$-Lysine as Hepatoma Cell-Targeted Gene Carrier", Bioconjugate Chem., 1998, pp. 708-718, vol. 9, Amerian Chemical Society.
Cortesi, et al., "Effecy of DNA Complexion and Freeze-Drying on the Physicochemical Characteristics of Cationic Liposomes", Antisense & Nucleic Drug Development, 2000, pp. 205-215, vol. 10, Mary Ann Liebert, Inc.
Katayose, et al., "Remarkable Increase in Nuclease Resistance of Plasma DNA through Supramolecular Assembly with Poly (ethylene glycol)-Poly ($_L$-lysine)", Journal of Pharmaceutical Sciences, 1998, vol. 87, No. 2, American Chemical Society and American Pharmaceutical Association.
Katayose, et al., "Water-Soluble Polyion Complex Associates of DNA and Poly (ethylene glycol)-Poly ($_L$-lysine) Block Copolymer", Bioconjugate Chem., 1997, pp. 702-707, American Chemical Society.
Kilcher, et al., "Influence of the DNA Complexation Medium on the Transfection Efficiency of Lipospermine/DNA Particles", Gene Therapy, 1998, pp. 855-860, vol. 5, MacMillan Press Ltd., Basingstoke, Great Britain.
Kwok, et al., "Strategies for Maintaining the Particle Size of Peptide DNA Condensates Following Freeze-Drying", International Journal of Pharmaceutics, 2000, pp. 81-88, vol. 203, No. 1-2, Elsevier Science B.V. Li, et al., "Lyophilization of Cationic Lipid-Protamine-DNA (LPD) Complexes", Journal of Pharmaceutical Sciences, 2000, pp. 355-364, vol. 89, No. 3, Wiley-Liss, Inc., & American Pharmaceutical Association.
Noel, et al., "High Compacted DNA—Polymer Complexes Via New Polynorbornene Polycationic Latexes With Acetate Counterion", SCISEARCH Database, 2000, pp. 8980-8983, vol. 16, No. 23, American Chemical Society, Washington, D.C.
Paxon, et al., "The Effect of Lyophilization on Plasmid DNA Activity", Pharmaceutical and Development Technology, 2000, pp. 115-122, vol. 5, No. 1, Marcel Dekker, Inc.

(Continued)

*Primary Examiner* — Scott Long
(74) *Attorney, Agent, or Firm* — Banner & Witcoff, Ltd.

(57) ABSTRACT

Counterions of polycations used to compact nucleic acids profoundly affect shape and stability of particles formed. Shape is associated with differential serum nuclease resistance and colloidal stability. A surrogate for determining such properties that is easy to measure is the turbidity parameter. Shape also affects the suitability and efficacy of compacted nucleic acid complexes for transfecting cells by various routes into a mammalian body. Moreover, counterions such as acetate can protect compacted nucleic acid complexes from adverse effects of lyophilization.

59 Claims, 24 Drawing Sheets

OTHER PUBLICATIONS

Toncheva, et al., "Novel vectors for gene delivery formed by self-assembly of NDA with poly (I-lysine) grafted with hydrophilic polymers", Biochemica et Biophysica Acta, 1998, pp. 354-368, Elsevier Science B.V.

Vinogradov, et al., "Self-Assembly of Polyamine-Poly (ethylene glycol) Copolymers with Phosphorothioate Oligonucleotides", Bioconjugate Chem., 1998, pp. 805-812, vol. 9, American Chemical Society.

Serres, et al., DNA Condensation and Transfection of Cells in Culture by a New Polynorbornane Polycationic Polymer, Langmuir 1999, pp. 6956-6950, vol. 15, American Chemical Society.

Wagner, et al., Direct Evidence for Counterion Release upon Cationic Lipid-DNA Condensation, Langmuir 2000, pp. 303-306, vol. 16, American Chemical Society.

Marschall, et al., Transfer of YACs up to 2.3 Mb intact into human cells with polyethylenimine, Gene Therapy, 1999, pp. 1634-1637, vol. 6.

Bloomfield, Current Opinion in Structural Biology, 1996, 6: 334-341.

Mel'nikov et al., J. Am. Chem. Soc. 1995, 117: 2401-2408.

Mel'nikov et al., J. Am. Chem. Soc. 1995, 117: 9951-9956.

Quong et al., Biotechnol. Bioeng. 1998, 60: 124-134.

Chong et al., Blochim. Biophys. Acta. 1976, 436: 260-282.

Cancellieri, et al., Biopolymers, 1974, 13: 735-743.

Ranganathan et al., Journal of Colloid and Interface Science, 1999, 214: 238-242.

McCluskie et al., Antisense & Nucleic Acid Drug Development, 1998, 8: 401-414, abstract only.

Hardy et al., Science, 1998, 282: 1075-1079.

Tresco et al., Advanced Drug Delivery Reviews, 2000, 42: 3-27.

Fischer, Cell. Mol. Biol., 2001, 47: 1269-1275.

Labhasetwar, Curr. Opin. Biotech., 2005, 16:1-7.

Bestor, J. Clin. Invest., 2000, 105: 409-411.

Kichler et al., Gene Therapy, 1998, 5: 855-860.

* cited by examiner

PROPERTIES OF VARIOUS PLASmin™ FORMULATIONS

| Formulation # | Counterion | Polylysine | PEG Content (%) | $t_{1/2}$ In Serum (h) | Turbidity Parameter | Sedimentation (%) |
|---|---|---|---|---|---|---|
| 1 | TFA | $CK_{15}$ | 40 | 11.6 | -1.5 | 30 |
| 2 |  |  | 60 | 10.8 | -3.0 | 66 |
| 3 |  |  | 80 | 9.4 | -2.4 | 42 |
| 4 |  |  | 100 | 16.7 | -1.3 | 11 |
| 5 | TFA | $CK_{30}$ | 40 | 8.1 | -1.4 | 44 |
| 6 |  |  | 60 | 4.1 | -3.2 | 79 |
| 7 |  |  | 80 | 3.4 | -4.0 | 117 |
| 8 |  |  | 100 | 2.6 | -4.3 | 90 |
| 9 | TFA | $CK_{45}$ | 40 | 6.3 | -3.3 | 78 |
| 10 |  |  | 60 | 4.4 | -3.8 | 82 |
| 11 |  |  | 80 | 4.8 | -3.3 | 84 |
| 12 |  |  | 100 | 5.0 | -3.9 | 89 |
| 13 | Acetate | $CK_{15}$ | 40 | 2.4 | -4.3 | 101 |
| 14 |  |  | 60 | 1.8 | -4.7 | 104 |
| 15 |  |  | 80 | 1.6 | -4.1 | 90 |
| 16 |  |  | 100 | 2.4 | -4.0 | 102 |
| 17 | Acetate | $CK_{30}$ | 40 | 1.8 | -4.1 | 99 |
| 18 |  |  | 60 | 2.4 | -4.3 | 91 |
| 19 |  |  | 80 | 2.2 | -4.4 | 108 |
| 20 |  |  | 100 | 4.0 | -4.4 | 109 |
| 21 | Acetate | $CK_{45}$ | 40 | 6.4 | -4.2 | 100 |
| 22 |  |  | 60 | 4.2 | -3.9 | 104 |
| 23 |  |  | 80 | 4.9 | -4.5 | 105 |
| 24 |  |  | 100 | 3.5 | -4.6 | 108 |

Fig. 9D

| Sample | Before Lyophilization | After Lyophilization |
|---|---|---|
| CK30TFA Original | | |
| 0.5M Sucrose | -4.31 | ppt |
| 0.5 M Trehalose | -3.81 | -4.10 |
| CK30P10k - TFA Original | -4.70 | -4.01 |
| 0.5M Sucrose | -4.51 | NE-4.61 |
| 0.5 M Trehalose | -4.15 | |
| CK30P10k - Acetate Original | -4.65 | -4.66 |
|  |  | -3.86 |
| 0.5M Sucrose | -4.76 |  |
| 0.5 M Trehalose | -4.56 | -3.32 |
|  | -4.57 | -4.39 |

Fig. 12

| Polylysine | Counterion | DNA Recovery | Turbidity Parameter |
|---|---|---|---|
| CK30P10k | Acetate | 100 | -4.2 |
| | Bicarbonate | 98 | -4.0 |
| | Chloride | 101 | -5.2* |
| | TFA | 97 | -4.6 |
| CK45P10k | Chloride | 105 | -4.0 |

Fig. 16

LYOPHILIZABLE AND ENHANCED COMPACTED NUCLEIC ACIDS

This application is a continuation of application Ser. No. 09/867,693, filed May 31, 2001, now abandoned, which claims the benefit of application Ser. No. 60/287,419 filed May 1, 2001 and No. 60/207,949 filed May 31, 2000, the disclosures of which are expressly incorporated herein.

BACKGROUND OF THE INVENTION

Despite the promise of preclinical models for systemic gene therapy to liver, lung, and other tissues, there is currently no commercial gene therapy product on the market. The failure of most human gene therapy clinical trials to treat metabolic disorders and cancer has been ascribed to the relative inefficiency of viral and non-viral gene transfer systems. Viral vectors have been used for most gene therapy studies because of their ability to efficiently infect cells in tissue culture. However, an enormous payload of particles needs to be applied in an intravenous injection to transduce cells in vivo, and toxicities of viral vectors are well documented [1], including a recent lethal toxicity that occurred following a portal vein injection of recombinant adenovirus [2]. In contrast, non-viral systems are generally felt to be safe although inefficient. There is a growing consensus that non-viral systems will be the vector of choice for in vivo applications once gene transfer efficiency is improved.

Several barriers restrict non-viral methods of gene transfer, including: i) particle stability in blood and interstitial tissues; ii) ability of the gene transfer particle to exit capillaries and travel to parenchymal cells; iii) cell entry via receptor-mediated endocytosis or cell fusion; iv) stability in and escape from endosomal and lysosomal compartments; v) diffusion rate in the cytoplasm; vi) nuclear pore transit; and vii) "uncoating" of DNA to permit biological function in the nucleus. For example, numerous publications have documented the failure of non-viral methods to transfect post-mitotic, growth-arrested cells [3-11], presumably because the intact nuclear membrane of non-dividing cells restricts entry of naked DNA into the nucleus via the 25 nm nuclear pore [12-13].

Thus there is a continuing need in the art for improved formulations and methods for delivery of genes to animals and humans. In addition, there is a need in the art for formulations which will be stable to storage and retain biological activity.

SUMMARY OF THE INVENTION

These and other objects of the invention are provided by one or more of the embodiments disclosed below. In one embodiment of the invention a method of estimating the colloidal stability of a preparation of compacted nucleic acids is provided. A turbidity parameter of a solution of compacted nucleic acid is determined. The turbidity parameter is defined as the slope of a straight line obtained by plotting log of apparent absorbance of light versus log of incident wavelength of the light. The wavelength used is between about 330 nm and 420 nm. A preparation is identified as colloidally stable if a turbidity parameter of less than −3 is determined. A preparation is identified as colloidally unstable if a turbidity parameter of greater than or equal to −3 is determined.

According to another aspect of the invention a non-naturally occurring composition comprising unaggregated nucleic acid complexes is provided. Each complex consists essentially of a single nucleic acid molecule and one or more polycation molecules. The polycation molecules have a counterion selected from the group consisting of acetate, bicarbonate, and chloride. The complex is compacted to a diameter which is less than (a) double the theoretical diameter of a complex of said single nucleic acid molecule and a sufficient number of polycation molecules to provide a charge ratio of about 1:1, in the form of a condensed sphere, or (b) 30 nm, whichever is larger. Optionally, the one or more polycation molecules of the unaggregated nucleic acid complexes are CK15-60P10, wherein acetate is used as a counterion. CK15-60P10 is a polyamino acid polymer of one N-terminal cysteine and 15-60 lysine residues, with a molecule of polyethylene glycol having an average molecular weight of 10 kdal attached to the cysteine residue.

According to another aspect of the invention a method of preparing a composition comprising unaggregated nucleic acid complexes is provided. Each complex consists essentially of a single nucleic acid molecule and one or more polycation molecules. The polycation molecules have a counterion selected from the group consisting of acetate, bicarbonate, and chloride. The complex is compacted to a diameter which is less than (a) double the theoretical diameter of a complex of said single nucleic acid molecule and a sufficient number of polycation molecules to provide a charge ratio of about 1:1, in the form of a condensed sphere, or (b) 30 nm, whichever is larger. The nucleic acid is mixed with the polycation having acetate, bicarbonate, or chloride as a counterion, at a salt concentration sufficient for compaction of the complex. Optionally, the one or more polycation molecules of the unaggregated nucleic acid complexes are CK15-60P10, wherein acetate is used as a counterion. CK15-60P10 is a polyamino acid polymer of one N-terminal cysteine and 15-60 lysine residues, with a molecule of polyethylene glycol having an average molecular weight of 10 kdal attached to the cysteine residue.

An additional embodiment of the invention is provided as a method of preparing a composition comprising unaggregated nucleic acid complexes. Each complex consists essentially of a single nucleic acid molecule and one or more polycation molecules. A nucleic acid molecule is mixed with a polycation molecule at a salt concentration sufficient for compaction of the complex to a diameter which is less than double the theoretical minimum diameter of a complex of said single nucleic acid molecule and a sufficient number of polycation molecules to provide a charge ratio of about 1:1, in the form of a condensed sphere, or 30 nm, whichever is larger. Unaggregated nucleic acid complexes are formed. Optionally, the one or more polycation molecules of the unaggregated nucleic acid complexes are CK15-60P10, wherein acetate is used as a counterion. CK15-60P10 is a polyamino acid polymer of one N-terminal cysteine and 15-60 lysine residues, with a molecule of polyethylene glycol having an average molecular weight of 10 kdal attached to the cysteine residue.

Also provided by the present invention is a non-naturally occurring composition comprising unaggregated nucleic acid complexes. Each complex consists essentially of a single nucleic acid molecule and one or more polycation molecules. The polycation molecules have a counterion selected from the group consisting of acetate, bicarbonate, and chloride. The nucleic acid molecule encodes at least one functional protein. Said complex is compacted to a diameter which is less than double the theoretical minimum diameter of a complex of said single nucleic acid molecule and a sufficient number of polycation molecules to provide a charge ratio of about 1:1, in the form of a condensed sphere, or 30 nm, whichever is larger.

Optionally, the one or more polycation molecules of the unaggregated nucleic acid complexes are CK15-60P10, wherein acetate is used as the counterion. CK15-60P10 is a polyamino acid polymer of one N-terminal cysteine and 15-60 lysine residues, with a molecule of polyethylene glycol having an average molecular weight of 10 kdal attached to the cysteine residue.

Another non-naturally occurring composition comprising unaggregated nucleic acid complexes is also provided. Each complex consists essentially of a single double-stranded cDNA molecule and one or more polycation molecules. Said polycation molecules have a counterion selected from the group consisting of acetate, bicarbonate, and chloride. The cDNA molecule encodes at least one functional protein. The complex is compacted to a diameter which is less than double the theoretical minimum diameter of a complex of said single cDNA molecule and a sufficient number of polycation molecules to provide a charge ratio of about 1:1, in the form of a condensed sphere, or 30 nm, whichever is larger. The nucleic acid complexes are optionally associated with a lipid. Optionally, the one or more polycation molecules of the unaggregated nucleic acid complexes are CK15-60P10, wherein acetate is used as the counterion. CK15-60P10 is a polyamino acid polymer of one N-terminal cysteine and 15-60 lysine residues, with a molecule of polyethylene glycol having an average molecular weight of 10 kdal attached to the cysteine residue.

Another non-naturally occurring composition comprising unaggregated nucleic acid complexes is provided by the present invention. Each complex consists essentially of a single nucleic acid molecule and one or more polycation molecules. The polycation molecules have a counterion selected from the group consisting of acetate, bicarbonate, and chloride. The nucleic acid molecule encodes at least one antisense nucleic acid. The complex is compacted to a diameter which is less than double the theoretical minimum diameter of a complex of said single nucleic acid molecule and a sufficient number of polycation molecules to provide a charge ratio of about 1:1, in the form of a condensed sphere, or 30 nm, whichever is larger. Optionally, the one or more polycation molecules of the unaggregated nucleic acid complexes are CK15-60P10, wherein acetate is used as the counterion. CK15-60P10 is a polyamino acid polymer of one N-terminal cysteine and 15-60 lysine residues, with a molecule of polyethylene glycol having an average molecular weight of 10 kdal attached to the cysteine residue.

According to another aspect of the invention a non-naturally occurring composition comprising unaggregated nucleic acid complexes is provided. Each complex consists essentially of a single nucleic acid molecule and one or more polycation molecules. The polycation molecule has a counterion selected from the group consisting of acetate, bicarbonate, and chloride. The nucleic acid molecule is an RNA molecule. The complex is compacted to a diameter which is less than double the theoretical minimum diameter of a complex of said single nucleic acid molecule and a sufficient number of polycation molecules to provide a charge ratio of about 1:1, in the form of a condensed sphere, or 30 nm, whichever is larger. Optionally, the one or more polycation molecules of the unaggregated nucleic acid complexes are CK15-60P10, wherein acetate is used as the counterion. CK15-60P10 is a polyamino acid polymer of one N-terminal cysteine and 15-60 lysine residues with a molecule of polyethylene glycol having an average molecular weight of 10 kdal is attached to the cysteine residue.

Another aspect of the invention provided here is a method of preparing a composition comprising unaggregated nucleic acid complexes. Each complex consists essentially of a single nucleic acid molecule and one or more polycation molecules. A nucleic acid molecule is mixed with a polycation molecule in a solvent to form a complex. The mixing is performed in the absence of added salt, whereby the nucleic acid forms soluble complexes with the polycation molecule without forming aggregates. Each complex consists essentially of a single nucleic acid molecule and one or more polycation molecules. The complexes have a diameter which is less than double the theoretical minimum diameter of a complex of the single nucleic acid molecule and a sufficient number of polycation molecules to provide a charge ratio of about 1:1, in the form of a condensed sphere, or 30 nm, whichever is larger. The polycation has acetate, bicarbonate, or chloride as a counterion. Optionally, the one or more polycation molecules of the unaggregated nucleic acid complexes are CK15-60P10, wherein acetate is used as the counterion. CK15-60P10 is a polyamino acid polymer of one N-terminal cysteine and 15-60 lysine residues with a molecule of polyethylene glycol having an average molecular weight of 10 kdal is attached to the cysteine residue.

Finally, the present invention provides a method of preventing or treating a disease or other clinical condition in a subject. A prophylactically or therapeutically effective amount of a composition is administered intramuscularly or to the lung. The composition comprises: unaggregated nucleic acid complexes, each complex consisting essentially of a single nucleic acid molecule and one or more polycation molecules, said polycation molecule having acetate, chloride, or bicarbonate as a counterion, wherein said complex is compacted to a diameter which is less than (a) double the theoretical minimum diameter of a complex of said single nucleic acid molecule and a sufficient number of polycation molecules to provide a charge ratio of about 1:1, in the form of a condensed sphere, or (b) 30 nm, whichever is larger. The nucleic acid is one whose integration, hybridization or expression within target cells of the subject prevents or treats the disease or other clinical condition. Optionally, the one or more polycation molecules of the unaggregated nucleic acid complexes are CK15-60P10, wherein acetate is used as the counterion. CK15-60P10 is a polyamino acid polymer of one N-terminal cysteine and 15-60 lysine residues with a molecule of polyethylene glycol having an average molecular weight of 10 kdal is attached to the cysteine residue.

The present invention thus provides the art with improved analytical and therapeutic techniques for delivery of DNA to cells by providing compacted nucleic acid compositions having improved stability and transfectability properties.

BRIEF DESCRIPTION OF THE DRAWINGS

FIG. 9D tabulates the results.

FIG. 12 shows assessment of the turbidity parameter before and after lyophilization using various excipients, counterions, and with or without polyethylene glycol. Sucrose and trehalose are very effective in maintaining the properties of the pre-lyophilization particles. PEG-acetate similarly was effective in maintaining the properties.

FIG. 16 shows a comparison of the colloidal stability of CK30P10K and CK45P10K DNA complexes compacted using various counterions in 0.9% NaCl. Colloidal stability is evaluated by sedimentation and turbidity parameter. The asterisk indicates that the value is lower than expected due to very low light scattering by this DNA formulation indicating that plasmid is not compacted, in agreement with electron microscopy and gel electrophoresis data.

FIG. 18 also shows the serum stability of the CK30P10K-DNA complexes with each of the different counterions. The lanes of the gel were loaded as follows: lane 1, DNA size markers; lane 2, naked DNA before compaction; lanes 3, 6, 9 and 12, compacted DNA; lanes 4, 7, 10 and 13, compacted DNA that was incubated in 75% mouse serum at 37° C. for 2 hours and trypsinized before loading; lanes 5, 8, 11 and 14, compacted DNA that was only trypsinized before loading.

DETAILED DESCRIPTION OF THE INVENTION

Figure 1:
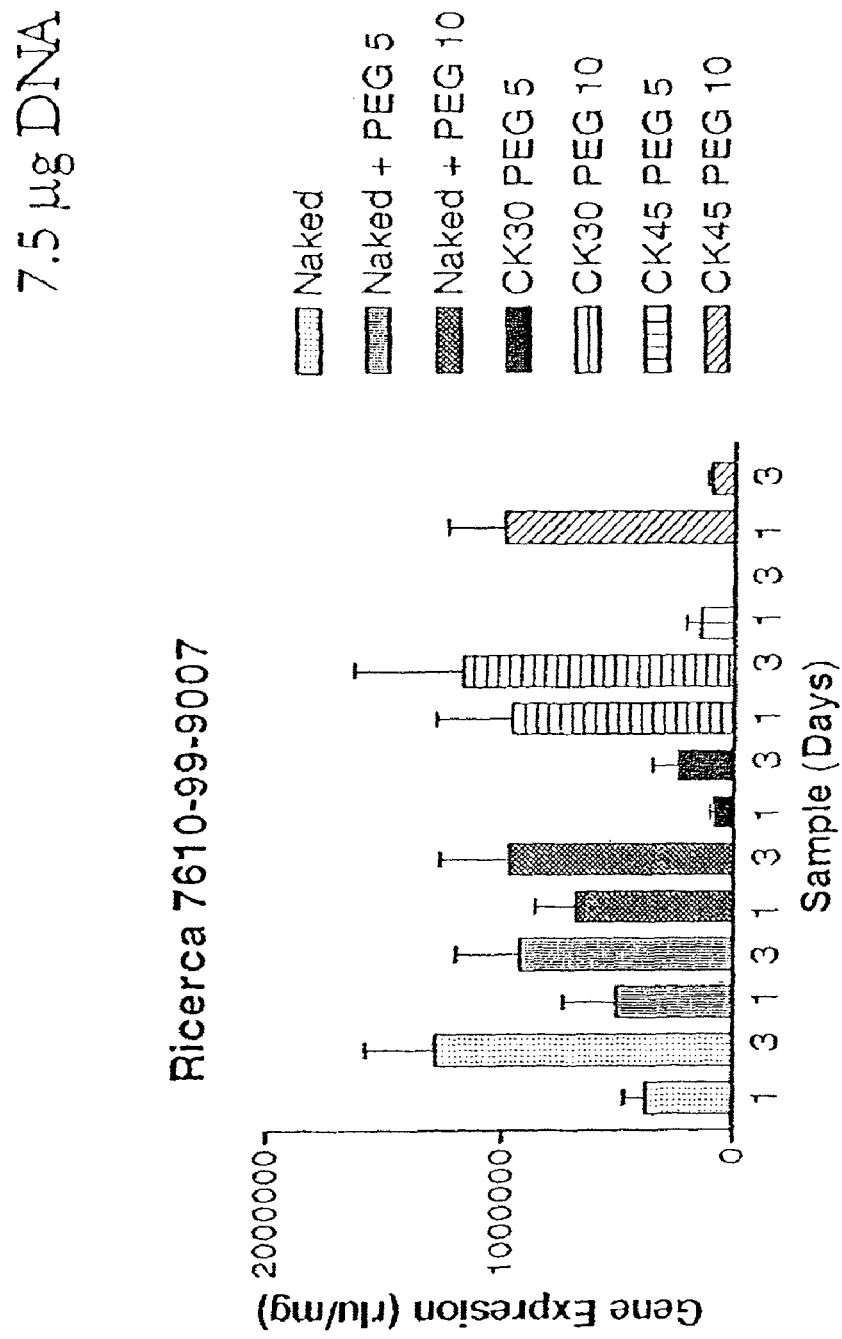
FIG. 1 shows intramuscular (IM) injection results using TFA (trifluoroacetate) and acetate as counterions for polylysine used to compact DNA.

The disclosures of U.S. Pat. Nos. 5,844,107, 5,877,302, 6,008,336, 6,077,835, 5,972,901, 6,200,801, and 5,972,900 and application Ser. No. 60/145,970, Ser. Nos. 09/722,340, 09/311,553 and No. 60/207,949 are expressly incorporated herein.

Counterions of polycations used to compact nucleic acids profoundly affect shape of particles formed. Shape is associated with differential serum nuclease resistance and colloidal stability. A surrogate for determining such properties which is easy to measure is the turbidity parameter. Moreover, shape affects the suitability and efficacy of compacted nucleic acid complexes for transfecting cells by various routes into a mammalian body.

The counterion used in making compacted nucleic acid complexes also has a significant effect on the stability of the complexes to lyophilization. Since lyophilization is a common process to render biologicals readily transportable and storage stable, this finding has significant ramifications. Typically, polyamino acid polymers contain trifluoroaceate (TFA) as a counterion. However, this counterion is far less beneficial than acetate for purposes of lyophilization of nucleic acid polymers, as shown below. Particles made using acetate retain their unaggregated nature, i.e., stay in solution better, after lyophilization and rehydration, retain their shape, and retain their gene transfer potential.

Particles according to the present invention contain nucleic acids, preferably a single nucleic acid molecule. The nucleic acid may be DNA or RNA, may be double or single-stranded, may be protein coding or anti-sense coding or non-coding. Nucleic acids also include analogs of RNA and DNA which are modified to enhance the resistance to degradation in vivo. A preferred analogue is a methylphosphonate analogue of the naturally occurring mononucleosides. More generally, the mononucleoside analogue is any analogue whose use results in oligonucleotides which have the advantages of (a) an improved ability to diffuse through cell membranes and/or (b) resistance to nuclease digestion within the body of a subject (Miller, P. S. et al., Biochemistry 20:1874-1880 (1981)). Such nucleoside analogues are well-known in the art. The nucleic acid molecule may be an analogue of DNA or RNA. The present invention is not limited to use of any particular DNA or RNA analogue, provided it is capable of fulfilling its therapeutic purpose, has adequate resistance to nucleases, and adequate bioavailability and cell take-up. DNA or RNA may be made more resistant to in vivo degradation by enzymes, e.g., nucleases, by modifying internucleoside linkages (e.g., methylphosphonates or phosphorothioates) or by incorporating modified nucleosides (e.g., 2'-O-methylribose or 1'-alpha-anomers). The methods used for forming the particles are as disclosed in U.S. Pat. Nos. 5,844,107, 5,877,302, 6,008,336, 6,077,835, 5,972,901, 6,200,801, and 5,972,900 and application Ser. No. 60/145,970, Ser. Nos. 09/722,340, 09/311,553 and No. 60/207,949.

Polycations according to the present invention preferably comprise polyamino acids such as polylysine and derivatives of polylysine. The polycation may contain from 15-60 lysine residues, preferably in the ranges of 15-30, 30-45, or 45-60 residues. Preferred derivatives of polylysine are CK15, CK30, CK45, which have an additional cysteine residue attached to polylysine polymers of length 15, 30, and 45 residues, respectively. Other amino acids can be readily attached to polylysine without departing from the spirit of the invention. Other polycationic amino acid polymers can be used such as polyarginine, or copolymers of arginine and lysine. Polymers of non-protein amino acids, such as ornithine or citrulline, could also be used. Any pharmaceutically approved or appropriate polycation can be used including but not limited to protamine, histones, polycationic lipids, putrescine, spermidine, spermine, peptides, and polypeptides. The polycation may also contain a targeting moiety, which is typically a ligand which binds to a receptor on a particular type of cell. The targeting ligand may be a polyamino acid or other chemical moiety. Specificity of interaction of the ligand and the receptor is important for purposes of targeting.

Conditions for making compacted nucleic acid particles are disclosed in the aforementioned patents and applications. The conditions may include from 0-1 M salt. The preferred salt is NaCl. Other chaotropic salts can be used as long as they are tolerated by the animal (or cells) to which they will be administered. Suitable agents include Sodium sulfate (Na$_2$SO$_4$), Lithium sulfate (Li$_2$SO$_4$), Ammonium sulfate ((NH$_4$)$_2$SO$_4$, Potassium sulfate (K$_2$SO$_4$), Magnesium sulfate (MgSO$_4$), Potassium phosphate (KH$_2$PO$_4$), Sodium phosphate (NaH$_2$PO$_4$), Ammonium phosphate (NH$_4$H$_2$PO$_4$), Magnesium phosphate (MgHPO$_4$), Magnesium chloride (MgCl$_2$), Lithium chloride (LiCl), Sodium chloride (NaCl), Potassium chloride (KCl), Cesium chloride (CaCl), Ammonium acetate, Potassium acetate, Sodium acetate, Sodium fluoride (NaF), Potassium fluoride (KF), Tetramethyl ammonium chloride (TMA-Cl), Tetrabutylammonium chloride (TBA-Cl), Triethylammoniym chloride (TEA-Cl), and Methyltriethylammonium chloride (MTEA-Cl).

If a Target Cell Binding Moiety (TBM) is used, it must bind specifically to an accessible structure (the "receptor") of the intended target cells. It is not necessary that it be absolutely specific for those cells, however, it must be sufficiently specific for the conjugate to be therapeutically effective. Preferably, its cross-reactivity with other cells is less than 10%, more preferably less than 5%.

There is no absolute minimum affinity which the TBM must have for an accessible structure of the target cell, however, the higher the affinity, the better. Preferably, the affinity is at least $10^3$ liters/mole, more preferably, at least $10^6$ liters/mole.

The TBM may be an antibody (or a specifically binding fragment of an antibody, such as an Fab, Fab, V$_M$, V$_L$ or CDR) which binds specifically to an epitope on the surface of the target cell. Methods for raising antibodies against cells, cell membranes, or isolated cell surface antigens are known in the art: (a). production of immune spleen cells: immunization with soluble antigens Hurrell, J. G. R. (1982) Monoclonal Antibodies: Techniques and Applications. CRC Press, Boca Raton, Fla. (b). immunization with complex antigens: membranes, whole cells and microorganisms. Hurrell, J. G. R. (1982) Monoclonal Antibodies: Techniques and Applications. CRC Press, Boca Raton, Fla. (c). production of monoclonal supernatants and ascites fluids. Andrew, S. M. and Titus, J. A. (1991). Purification of Immunoglobulin G. in Current Protocols in Immunology (J. E. Coligan, A. M. Kruisbeek, D. H. J. Margulies, E. M. Shevach and W. Strober, ed.) pp. A.3.9-A.3.12. Greene Publishing Wiley-Interscience, New York. (d). production of polyclonal antiserum in rabbit. Garvey J. S., Cremer, N. E. and Sussdorf, D. H (eds) (1977) Methods in Immunology: A Laboratory Text for Instruction and Research, Third Edition. W. A. Benjamin, North Hampton, Mass. (e). production of anti-peptide antibodies by chemical coupling of synthetic peptides to carrier proteins Jemmerson, R., Morrow, P. I., Klinman, N. I and Patterson, Y. (1985). Analysis of an evolutionary conserved site on mammalian cytochrome C using synthetic peptides. Proc. Natl. Acad. Sci, U.S.A. 82, 1508-1512.

The TBM may be a lectin, for which there is a cognate carbohydrate structure on the cell surface. The target binding moiety may be a ligand which is specifically bound by a receptor carried by the target cells. One class of ligands of interest are carbohydrates, especially mono- and oligosaccharides. Suitable ligands include galactose, lactose and mannose. Another class of ligands of interest are peptides (which here includes proteins), such as insulin, epidermal growth factor(s), tumor necrosis factor, prolactin, chorionic gonadotropin, FSH, LH, glucagon, lactoferrin, transferrin, apolipoprotein E, gp120 and albumin. The following table lists preferred target binding moieties for various classes of target cells:

| Target Cells | Target Binding Moiety |
|---|---|
| liver cells | galactose |
| Kupffer cells | mannose |
| macrophages | mannose |
| lung | Fab fragment vs. polymeric immunoglobulin receptor (Pig R) |
| adipose tissue | insulin |
| lymphocytes | Fab fragment vs. CD4 or gp120 |
| enterocyte | Vitamin B12 |
| muscle | insulin |
| fibroblasts | mannose-6-phosphate |
| nerve cells | Apolipoprotein E |

Use of a target binding moiety is not strictly necessary in the case of direct injection of compacted nucleic acid complex. The target cell in this case is passively accessible to the compacted complex by the injection of the complex to the vicinity of the target cell. Target binding moieties can be attached to lysine residues, cysteine residues, or PEG using covalent or non-covalent interactions.

It has been found that the counterion provided in association with the polycation profoundly affects shape, and that shape is associated with physiologically important properties for delivery of nucleic acids. For example, trifluoroacetate (TFA) particles form spheroids and short rods of less than about 50 nm. Acetate leads to longer rods of 100 to 200 nm.

Chloride leads to particles which are longer and skinnier than acetate particles. Bicarbonate leads to a mixture of rods of 100-200 nm and toroids. Any physiologically and pharmacologically acceptable counterion can be used with the polycation. Bromine is typically supplied with reagent grade polylysine. It is believed that bromine is inferior to other cations as described herein, especially with respect to physiological acceptability. Counterions can be supplied to or substituted on polycations by means of chromatography or dialysis, for example. For example, the polycation can be bound to an ion exchange resin and eluted with the desired counterion. Any method known in the art can be used for this purposed. Interestingly, it has been found that once a particle has been compacted into a particular shaped particle, removal and replacement of the counterion, such as by dialysis, does not significantly alter the shape once assumed. Thus a favorable shape can be obtained with a particle using a non-optimum counterion for physiological purposes and the counterion can be replaced with a superior counterion, while retaining the shape obtained during compaction with the original counterion. The favorable affects on nucleic acids of the counterions may not require compaction. Thus the polycations and counterions can be used with non-compacted nucleic acids as well.

The behavior of these different shaped particles in gene delivery in animals varies significantly. Acetate particles are superior, for example, to TFA particles for delivery to muscle and lung. Delivery to other locations in the body may also be accomplished. These include, without limitation, administrations which are intratracheal, by inhalation, intradermal, topical, by eyedrops, subcutaneous, intrathecal, by enema, enteral, intravenous, intraarterial, intralymphatic, intraperitoneal, intrapleural, intravesicular, intraarticular, intracardiac, intracranial, intratumor, direct to an organ, by eardrops, by nosedrops, intraurethral, endoscopically to the upper gastrointestinal tract, to the sigmoid, or to the colon, by cystoscopy, by thorascope, by arthroscope, by mediastinoscopy, by endoscopic retrograde chlolangiopancreatography, by Omaya reservoir, by angiography including cardiac catheterization and cerebral angiography, intrauterine, intravaginal, to the bone marrow, to hair follicles, to the vitreous and aqueous humor, to the sinuses, to the ureter/pelvis of the kidney, to the fallopian tube, and to lymph nodes.

The complexes have a diameter which is less than double the theoretical minimum diameter of a complex of the single nucleic acid molecule and a sufficient number of polycation molecules to provide a charge ratio of about 1:1, in the form of a condensed sphere. For the purposes of this invention, "about 1:1" encompasses from 1.5:1 to 1:1.5.

Turbidity parameter can be assessed by determining the absorbance of a composition. In a preferred embodiment a Zeiss MCS501 UV-Vis spectrometer is used. Other spectrometers as are known in the art can be substituted. Suitable wavelengths for collection absorbance measurements are between about 330 nm and 420 nm.

The invention is explained in particular applications in the examples which follow.

EXAMPLES

Example 1

Figure 8:
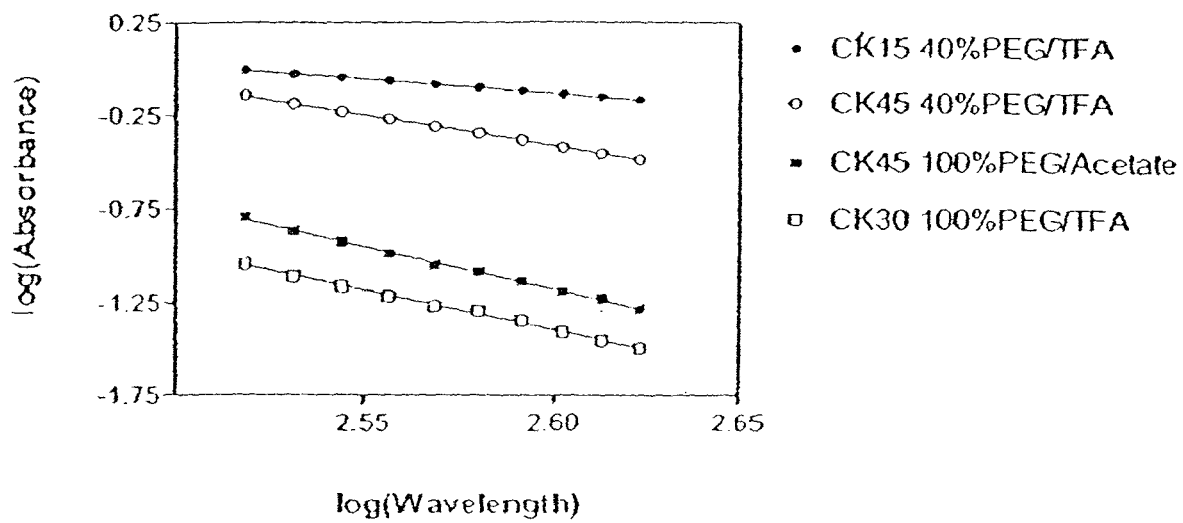
FIG. 8 shows turbidity parameter plots as a function of size of polylysine used in compaction and counterion
Figure 9A:
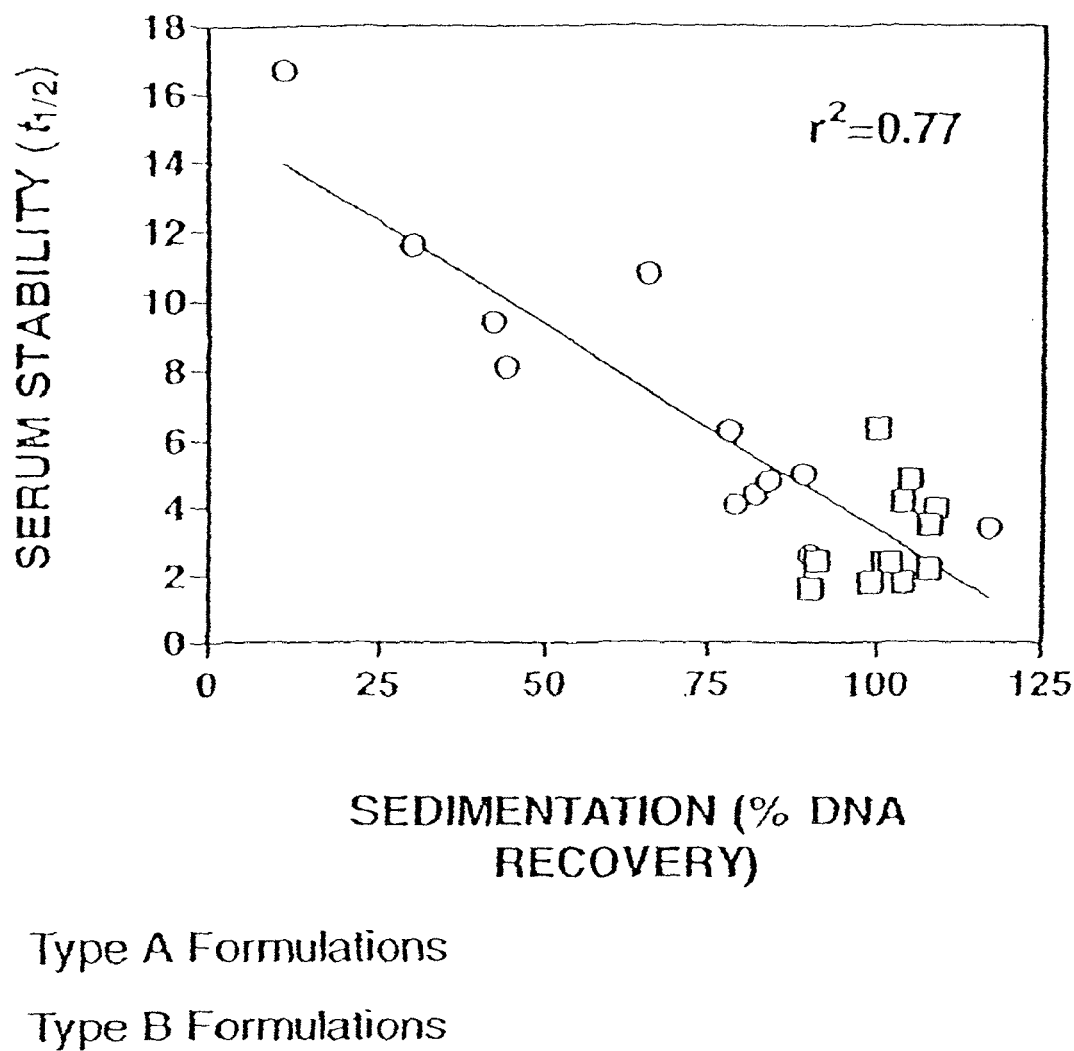
FIG. 9A, FIG. 9B, and FIG. 9C show a comparison of serum stability, turbidity parameter, and sedimentation, for various formulations of compacted nucleic acids.
Figure 9B:
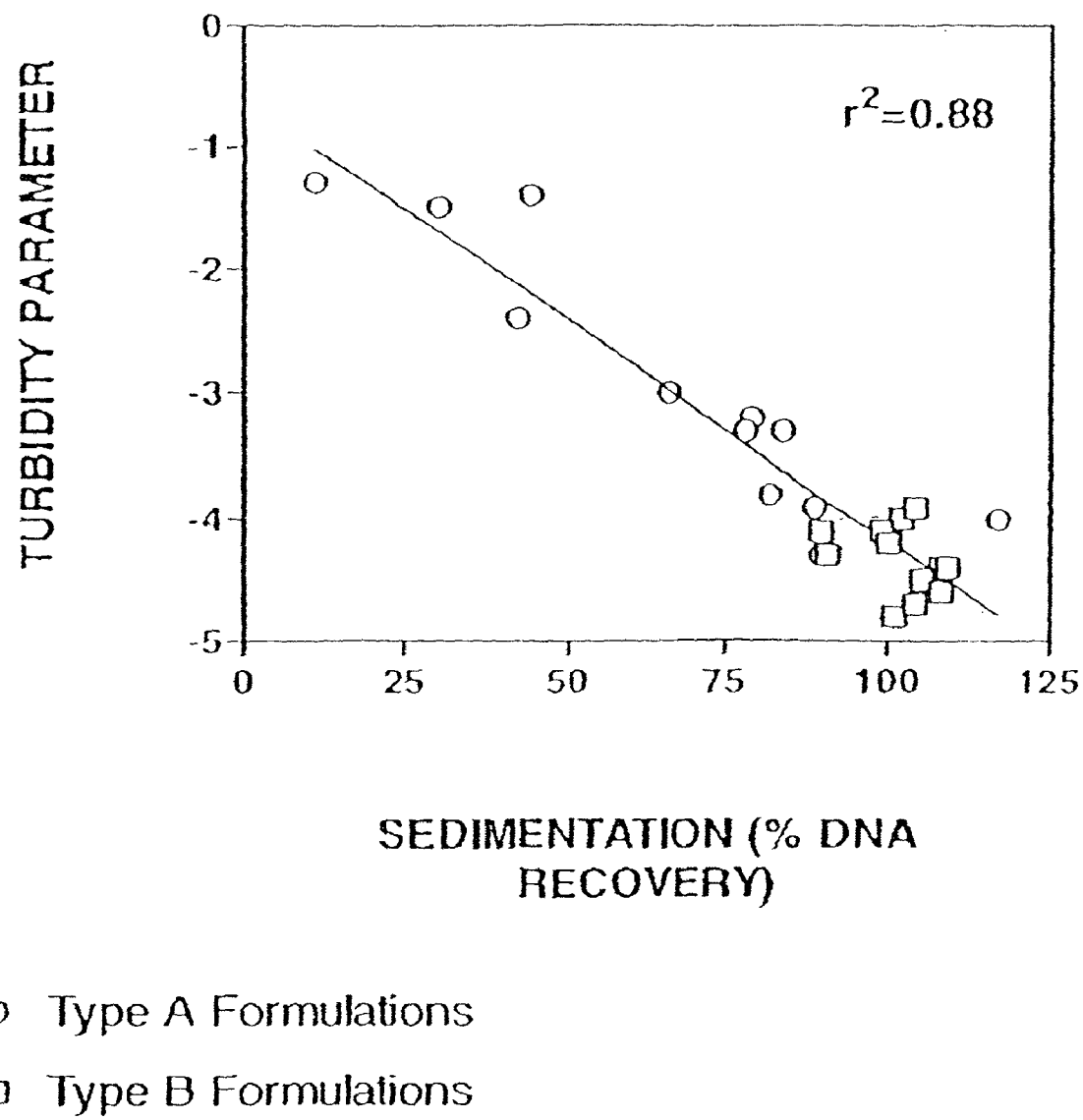
Figure 9C:
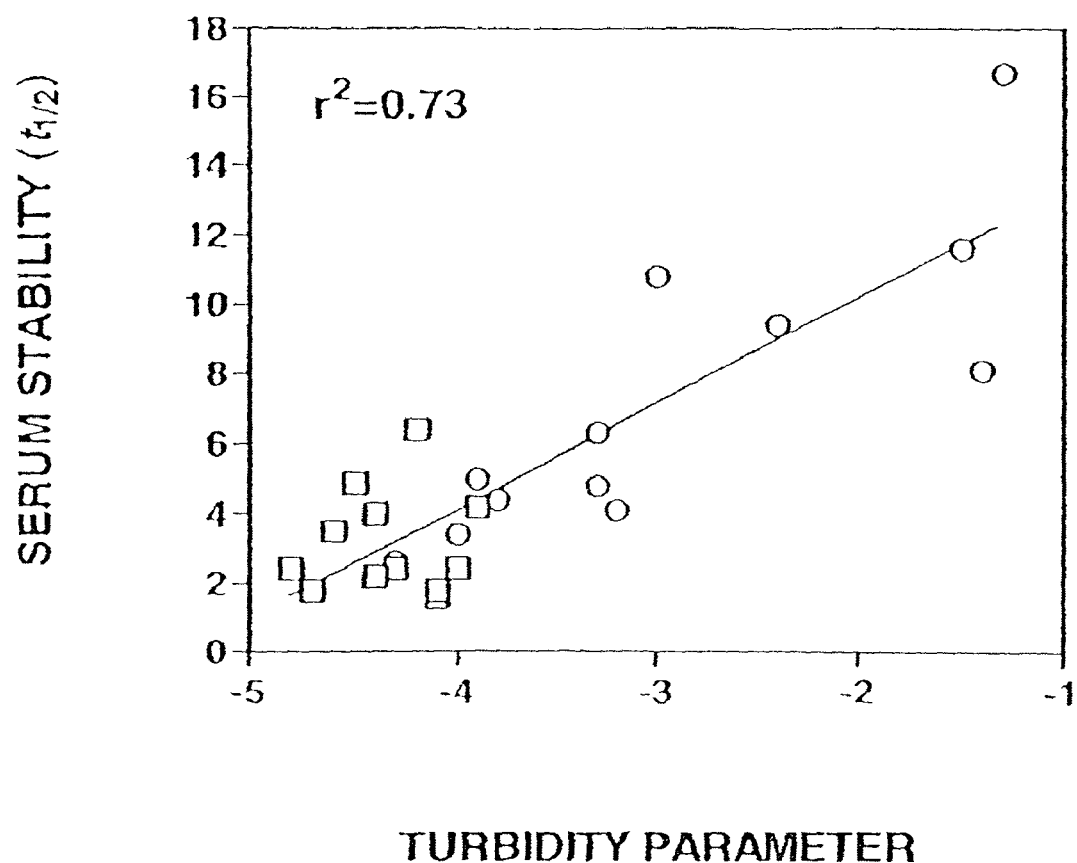
Figure 10:
FIG. 10 shows the influence of counterion on the morphology of PEG-substituted CK30 compacted DNA as shown under the electron microscope.
Figure 10:
Figure 10:
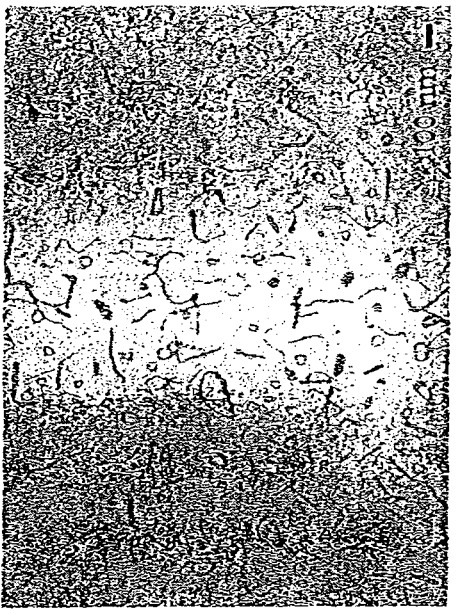
Figure 10:
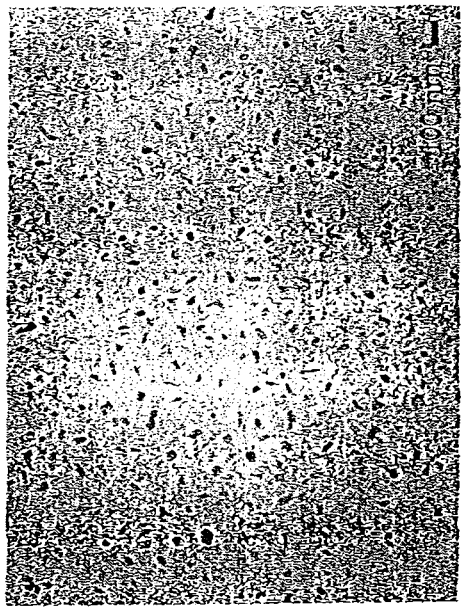
Figure 17:
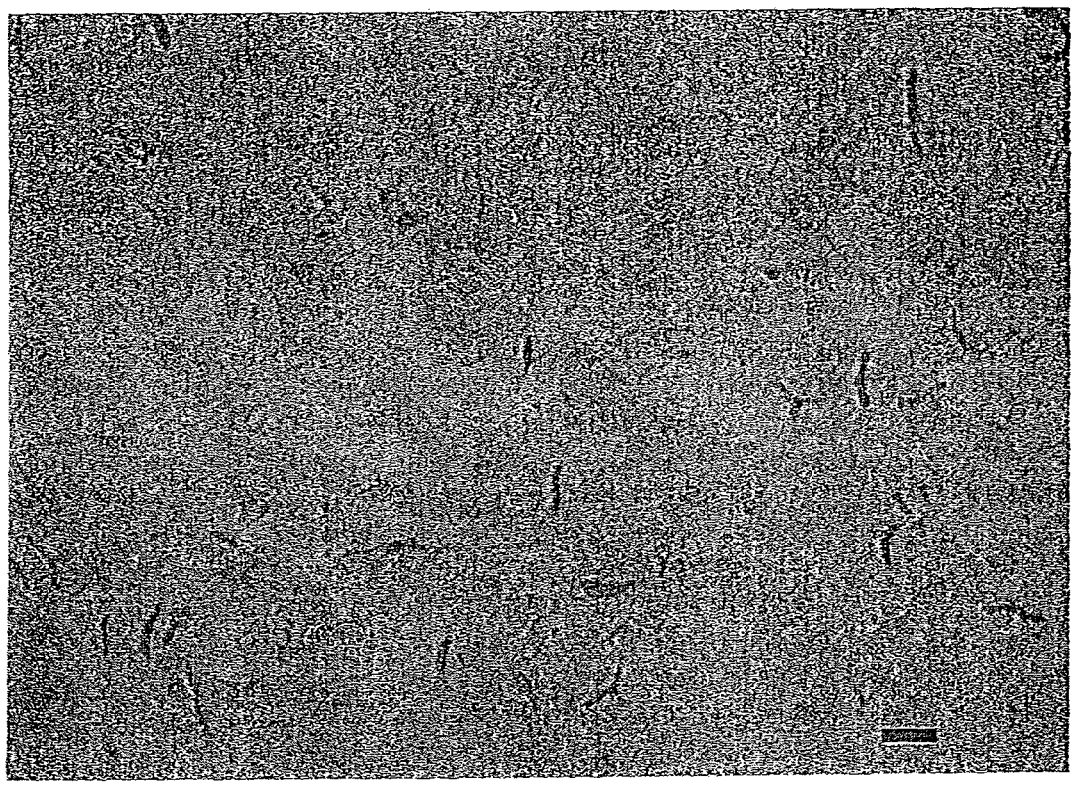
FIG. 17 shows an electron micrograph of plasmid DNA compacted by CK45P10 with chloride as a counterion. Magnification 40,000. The bar shows 100 nm.

Resistance to serum nucleases is, among other properties, an important feature of any effective gene therapy vector designed to be administered systemically. Ideally, engineering this resistance should not compromise other desirable properties of a vector, such as its small size and colloidal stability. We have developed reagents and methods that permit us to reproducibly compact plasmid DNA with polylysine-polyethylene glycol (PEG) conjugates to form small particles having defined morphology (PLASmin™ DNA complexes). Some of these formulations are stable in serum and do not aggregate in physiologic saline. By changing components and conditions of the compaction procedure, size and shape of the particles can be modified. To evaluate potential correlations between serum stability and the physical state of PLASmin™ DNA complexes, we have prepared a matrix of 24 formulations using polylysines of various lengths and substituted with PEG to various extents. FIG. 9D. Polylysines having exactly 15, 30, and 45 residues were obtained by solid-phase synthesis. These polymers contained an N-terminal cysteine residue that was used to conjugate PEG. Various mixtures of PEG-substituted and non-substituted polylysines were used to obtain different PLASmin™ DNA complexes. Stability of the complexes in 75% mouse serum was tested by incubating compacted DNA at 37° C. for up to 5 days and determining half-life of DNA degradation. Simultaneously, physical characteristics of the complexes in 150 mM NaCl were determined. Morphology was visualized by transmission electron microscopy (FIG. 10 and FIG. 17). DNA condensed with acetate and bicarbonate salts of CK30 polylysine assumed forms of long (100-300 nm) and narrow (10-20 nm) rods and relaxed toroids (~50-100 nm diameter, 10-20 nm width); the TFA salt resulted in much shorter rods (<60 nm by 20-30 nm) and small globules (20-30 nm); the chloride form of CK30 did not compact DNA at all (FIG. 10), while CK45/chloride (FIG. 17) gave results similar to CK30/acetate. Colloidal instability (tendency to aggregate) was evaluated by a sedimentation assay. Additionally, light scattering of solutions containing PLASmin™ DNA complexes was measured and expressed as a turbidity parameter (FIG. 8). We found that all PLASmin™ DNA complexes (FIG. 9A) were much more stable in serum than naked DNA. The half-life for compacted DNA ranged from ~2-17 hr, while naked DNA was completely digested within a few minutes. We also found a correlation ($r^2$=0.77) between half-life of degradation and colloidal instability of PLASmin™ DNA complexes: particles that tended to aggregate were more resistant to nucleases. The tendency to aggregate also correlated with morphology of the complexes: rod-like complexes did not aggregate; thus, they all showed very similar serum stability, independent of their composition ($t_{1/2}$~2-5 hr). In contrast, spherical complexes showed various extents of tendency to aggregate depending on polylysine chain-length and PEG content. There was little difference in serum stability between small globules and rod-like particles. In agreement with the prediction that aggregated particles should scatter various light wavelengths differently than small complexes, we found a good correlation ($r^2$=0.88) between colloidal instability of PLASmin™ DNA complexes and turbidity of their solutions (FIG. 9B): stable complexes had turbidity parameter around −4 to −5 (in accordance with the Rayleigh law), while for the largest and least stable particles this value increased to −1.3. Consequently, the turbidity parameter also correlated with the half-life of DNA degradation in serum ($r^2$=0.73; FIG. 9C). Thus, we conclude that the turbidity parameter, which is easy to determine, can be conveniently used to preliminarily screen various formulations of compacted DNA and predict their colloidal stability as well as serum stability.

Example 2

Effective gene transfer to lung would facilitate therapies for pulmonary diseases, such as cystic fibrosis, and may provide a potent means for administering mucosal vaccines.

Figure 6:
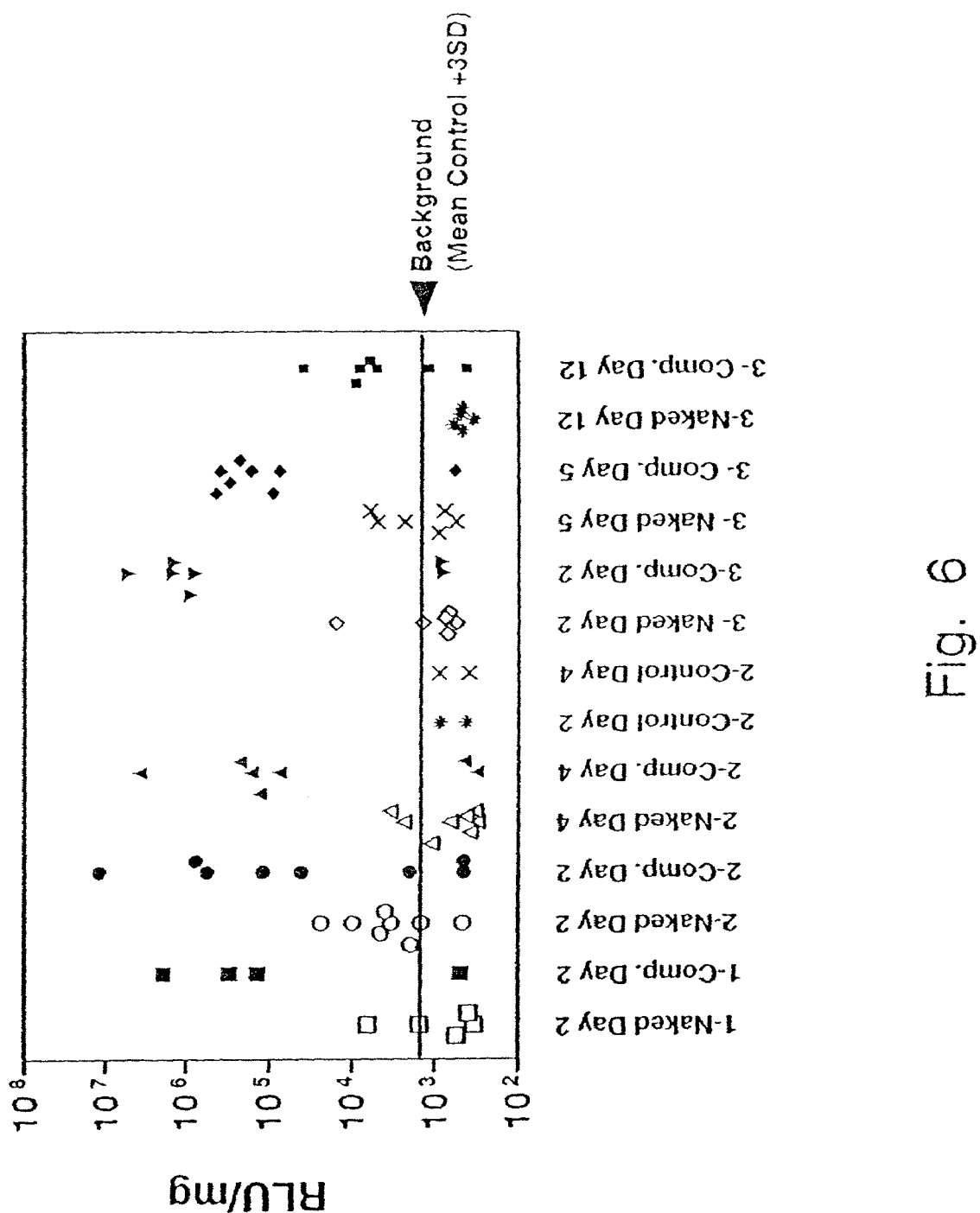
FIG. 6 shows intra-tracheal instillation of 100 ug naked and 100 ug compacted DNA compared as to amount of expression in the lung of the instilled gene (luciferase) as a function of time after gene transfer.
Figure 7A:
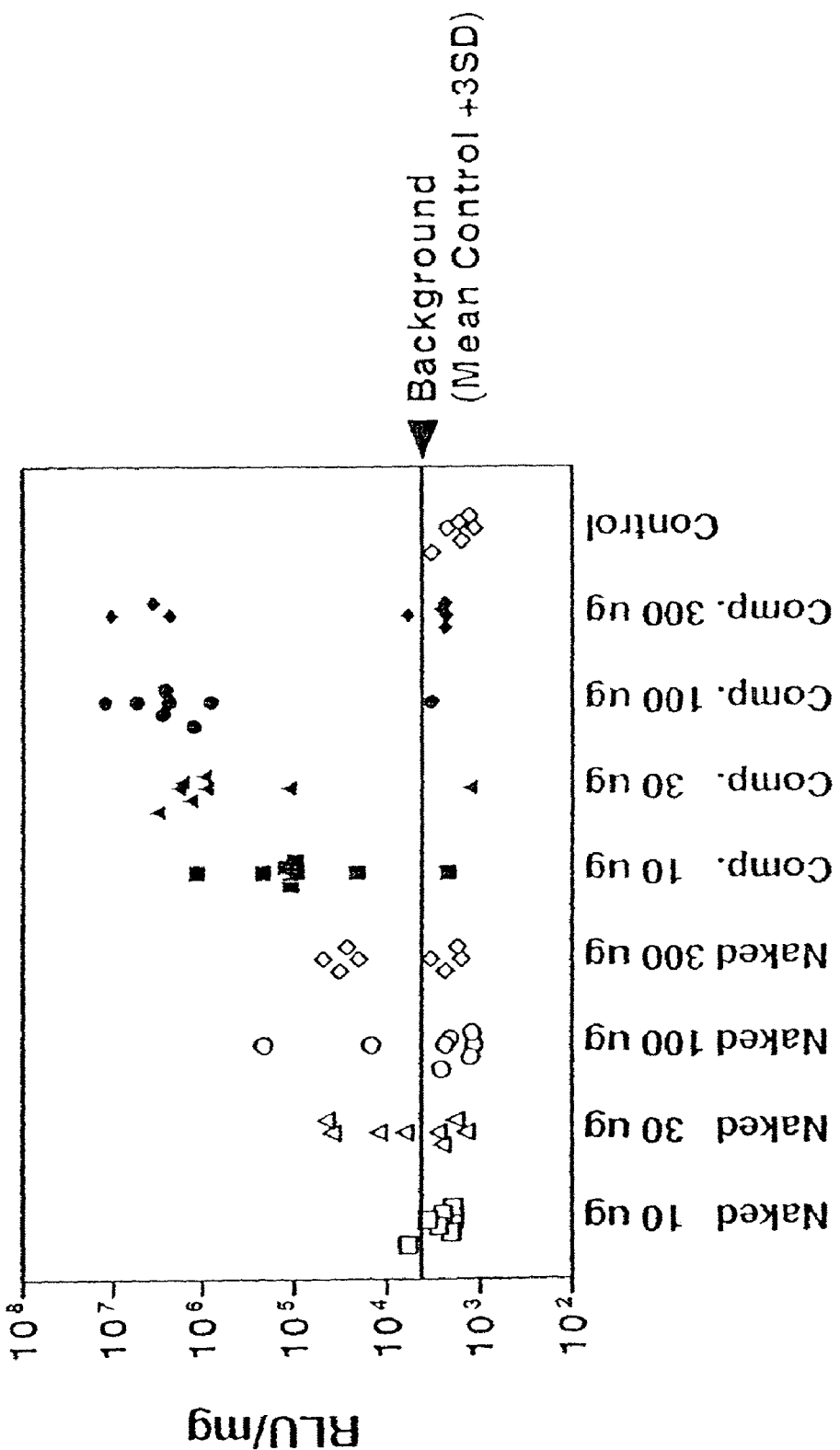
FIG. 7A shows intra-tracheal installation of naked and compacted DNA compared as to amount of expression in the lung of the instilled gene (luciferase) as a function of time after gene transfer.
Figure 7B:
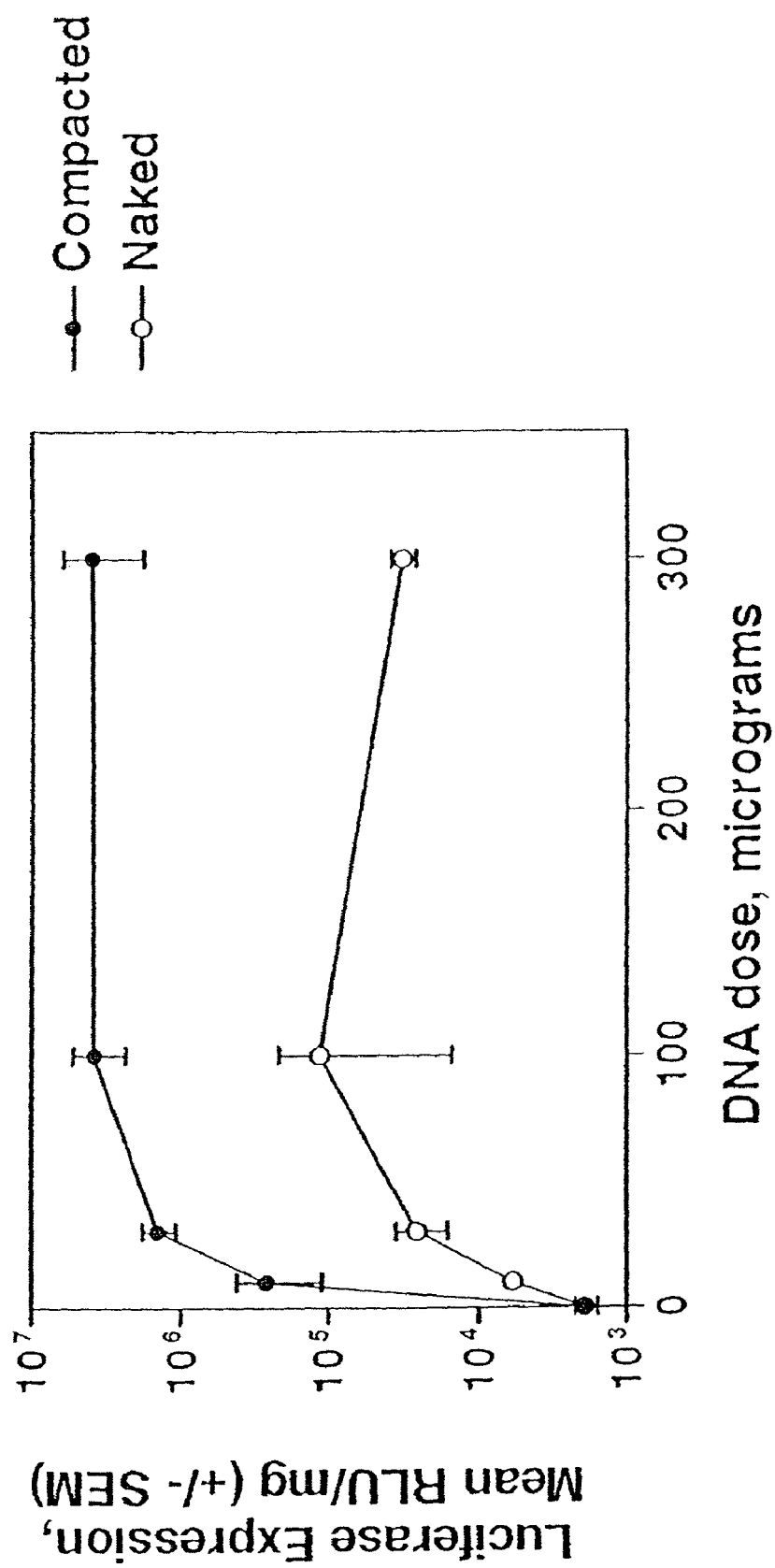
FIG. 7B shows plot of data above background from FIG. 7A.

Although direct instillation of naked DNA into mouse airways generates measurable transgene expression, the level of expression is low, and the duration of expression is short. We have developed reagents and formulation methods that compact single molecules of plasmid DNA into 20-25 nm particles (PLASmin™ DNA complexes). Unlike naked DNA, these complexes are protected from nuclease digestion and are stable in serum. Additionally, PLASmin™ DNA complexes do not aggregate in physiologic saline and can be concentrated to over 12 mg/ml of DNA. To determine if PLASmin™ DNA complexes would generate significant levels of gene expression in lung, we instilled naked and PLASmin™ DNA complexes into the lungs of C57BL/6J mice via direct intratracheal administration. These compacted particles consisted of plasmid DNA and PEG-substituted polylysine polymers consisting of 30 lysine residues. The plasmid construct encoded a luciferase reporter gene transcriptionally controlled by a CMV enhancer, an elongation factor 1-alpha (EF1-alpha) promoter, EF1-alpha intron 1, the RU5 translational enhancer from HTLV I, and an SV40 late polyadenylation signal. A DNA dose of 100 ug was administered in 25 or 50 ul of 150 mM NaCl. At 2, 4, 5, or 12 days following gene transfer, extracts were prepared from both lungs and luciferase activity was measured as relative light units per mg of protein (FIG. 6). Whereas naked DNA generated a signal of approximately 4,000 RLU/mg on day 2 and 1,100 RLU/mg on day 4, PLASmin™ DNA complexes generated approximately 1,100,000 RLU/mg on day 2, and 630,000 rlu/mg on day 4. Gene expression persisted for at least 12 days after gene transfer, although at lower levels. These compacted DNA particles produced 400-fold enhanced gene expression compared to naked DNA on day 2, and over 1,300-fold improved gene expression on day 4. In contrast to whole lung extracts, less gene expression was noted in trachea, and no expression in liver (data not shown). In dose response studies, peak levels of transgene expression was observed using a 100 ug dose (FIG. 7). In summary, we have determined that PLASmin™ DNA complexes effectively deliver and express transgenes in mouse lung following direct intra-tracheal administration. In studies in progress, the beta-galactosidase reporter gene is being utilized to define the cell type(s) being transfected. PLASmin™ DNA complexes may provide an appropriate gene transfer method for diverse pulmonary diseases and/or mucosal vaccines.

Example 3

Gene transfer in muscle cells following an intramuscular injection provides a means of safe and effective vaccination, and provides therapeutic levels of recombinant proteins, such as factor IX, factor VIII, or alpha-1 anti-trypsin.

Figure 2:
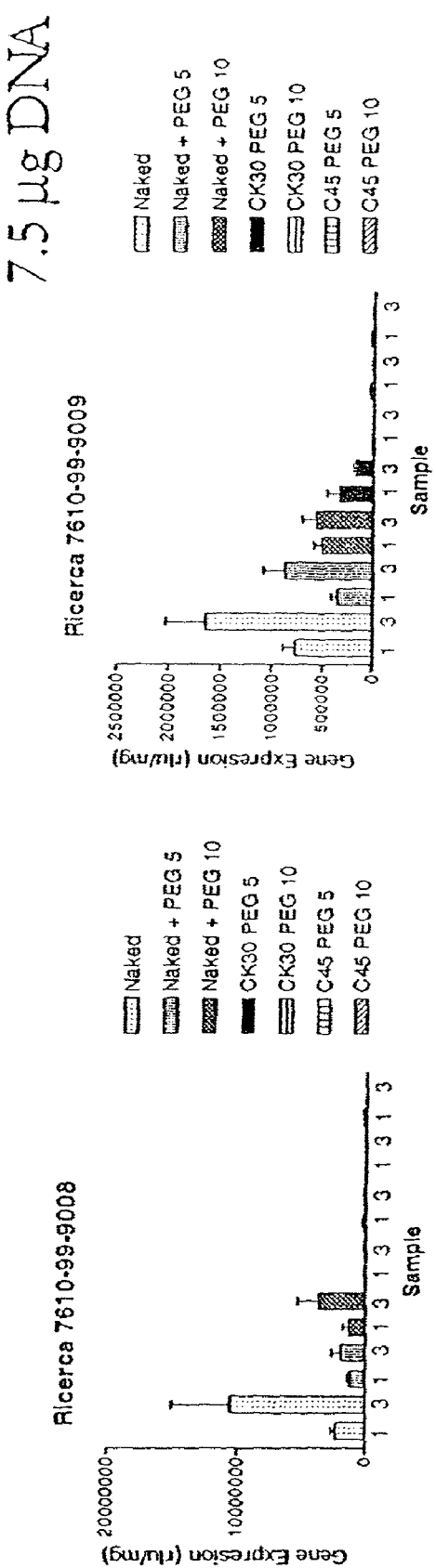
FIG. 2 shows intramuscular injection results using TFA (trifluoroacetate) as counterion for polylysine used to compact DNA.
Figure 3:
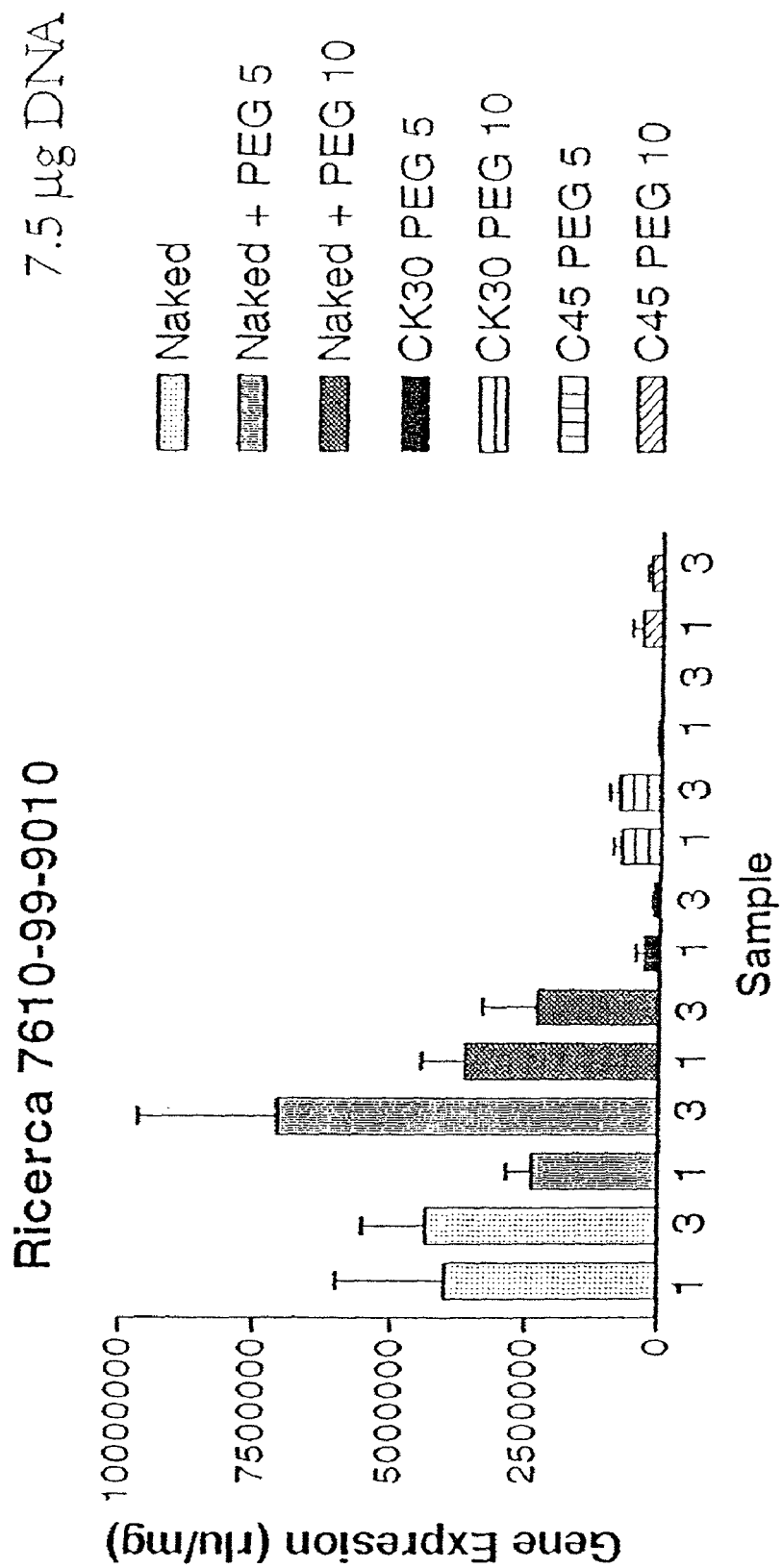
FIG. 3 shows intramuscular injection results using acetate as counterions for polylysine used to compact DNA.
Figure 4:
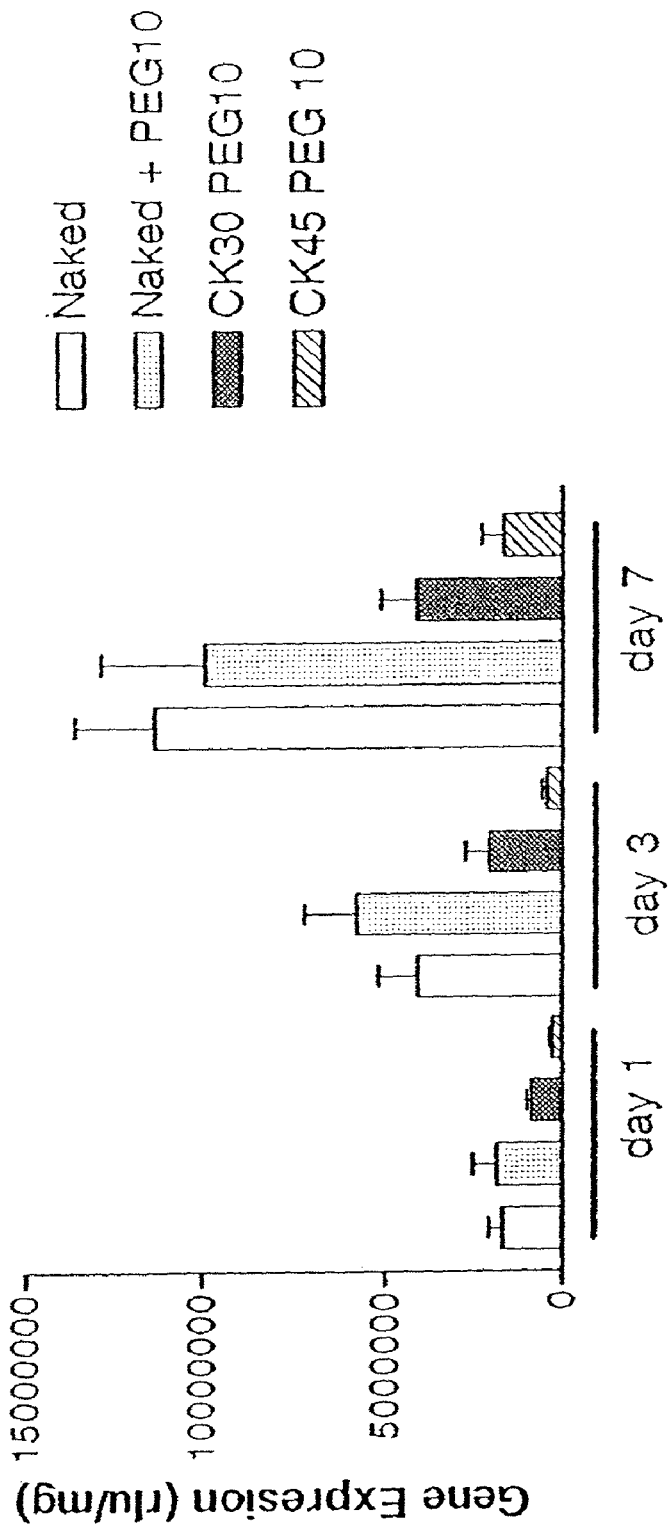
FIG. 4 shows intramuscular injection results using acetate as counterions for polylysine used to compact DNA.
Figure 5:
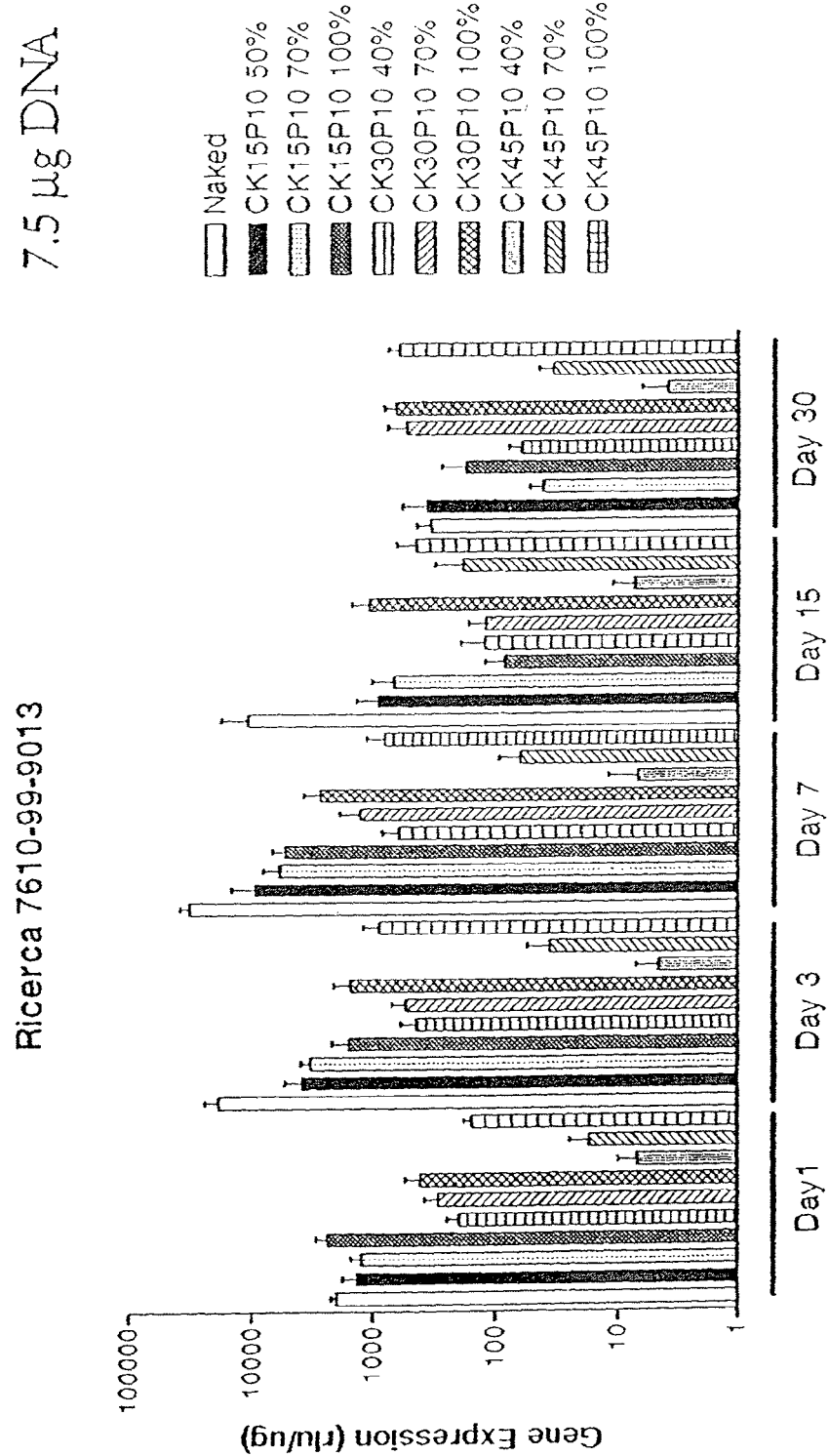
FIG. 5 shows a variety of parameters varying and their effectiveness in IM injections, including size of polylysine (CK), polyethylene glycol substitution.

To optimize formulations of PLASmin™ DNA complexes for intramuscular administration, various preparation of compacted DNA encoding the luciferase reporter gene were administered to CD2 mice by single injection in the tibialis anterior muscle. Gene expression was assayed at various days post gene transfer and is presented as relative light units (RLU)/mg protein. In FIG. 1, expression of compacted DNA formulated with the acetate salt of CK30 polycation (complexed with PEG 10 kD) was enhanced, as measured by luciferase activity on both days 1 and 3, compared to other preparations of DNA formulated with the TFA salt of CK30 or CK45. To define further the roles of counterion type, length of polylysine, and percent substitution of polyethylene glycol (PEG), additional experiments were conducted. Animals received IM injections of TFA complexes consisting of either CK30 or CK45, and PEG sizes of either 5 or 10 kD. FIG. 2) Luciferase activity was significantly less than that observed for CK30, PEG 10 kD, acetate complexes in FIG. 1. The enhanced gene expression of complexes prepared using the acetate salt of CK30, PEG 10 kD, was confirmed. (FIG. 3) In this experiment, the CK30 polycation generated better luciferase activity than the CK45 polymer, and CK30 yielded higher levels of luciferase activity when complexed with 10 kD rather than 5 kD PEG. The duration of gene expression produced by acetate complexes consisting of either CK30 or CK45, both complexes with PEG 10 kD, were next evaluated, and the results are shown in FIG. 4. In this study, the CK30 polycation gave the best level of reporter gene activity, and the level of activity was better on day. 7 than days 1 or 3. A variety of acetate complexes were tested for gene activity as shown in FIG. 5. These formulations included CK15, CK30, and CK45 polycations complexed with various percentages of PEG 10 kD. A time course to 30 days was performed. Although gene expression on days 1, 3, and 7 appeared better using CK15 compared to CK30, the particle sizes of some CK15 complexes were larger than 30 nm or two times the theoretical diameter of a complex of said single nucleic acid molecule and a sufficient number of polycation molecules to provide a charge ratio of about 1:1, in the form of a condensed sphere. For days 1, 3, 7, and 15, at least one preparation of CK30 compacted DNA was superior to any CK45 preparation. For CK30, the 100% PEG 10 kD complexes generated better reporter gene activity than either the 70% or 40% substitutions. In summary, the best formulation of compacted DNA in these studies was the acetate salt of CK30 polycation having a 100% substitution with PEG 10 kD.

Example 4

Prior to injection, animals are anesthetized by intraperitoneal injection with a rodent cocktail of ketamine, xylazine, and acepromazine. A volume of 150 ul anesthetic is administered per mouse, at a concentration of 21.5 mg/ml ketamine, 10.7 mg/ml xylazine, and 0.36 mg/ml acepromazine. The final dose is 0.32 mg ketamine, 1.6 mg xylazine, and 0.054 mg acepromazaine per mouse.

A volume of 25 ml of each plasmid DNA formulation is administered intratracheally to each animal using a 22-gauge needle. A plastic catheter is placed in the trachea of the mice via a percutaneous approach. The resulting does per animal is 300 ug, 100 ug, 30 ug, and 10 ug DNA per mouse.

After injection, animals are anesthetized by carbon dioxide and sacrificed. The animals are bled and rinsed intra-arterially with phosphate buffered saline. The lungs, trachea, and liver are isolated and rinsed in the saline. Tissue samples are immediately frozen on liquid nitrogen, and then stored at −70° C.

Lung tissue is homogenized using Polytron in lysis buffer. Protein concentration is determined. Luciferase activity of the homogenates is determined by luciferase assay.

Example 5

Figure 11:
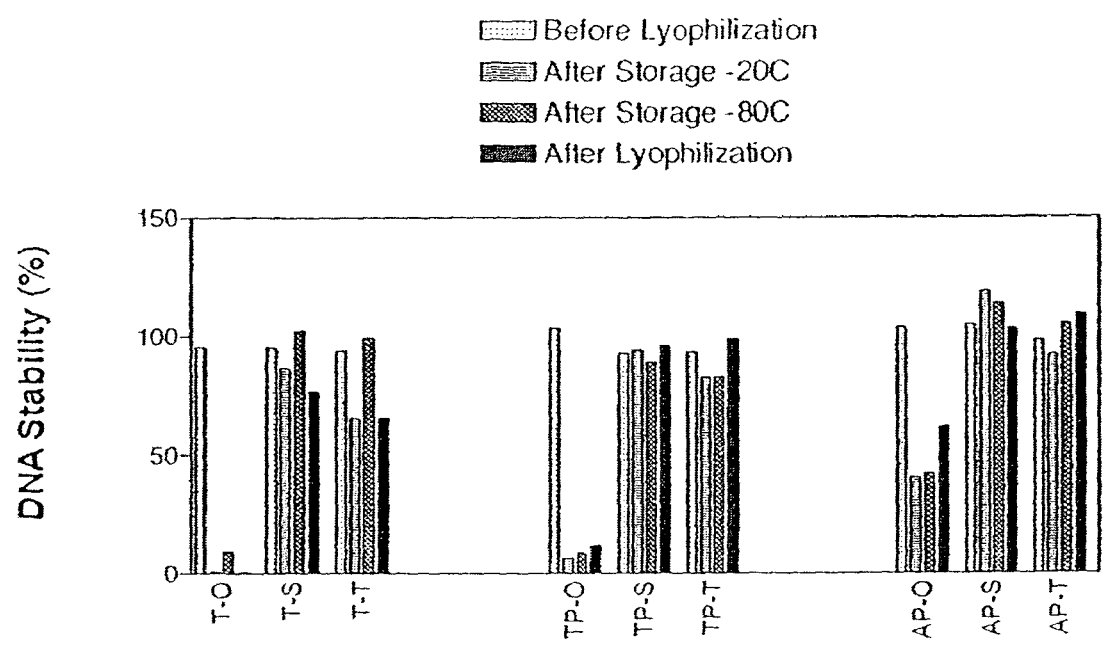
FIG. 11 shows the stability of PLASmin™ DNA complexes upon freezing and lyophilization. Particles were tested with sucrose, trehalose, or no excipient. Particles were tested with and without polyethylene glycol, and with TFA or acetate as the counterion. DNA stability was assessed by a low (3400×g×1 min) spin to pellet aggregates, and monitoring the absorbance of DNA in the supernatant. Stability with acetate as the counterion surpassed other formulations in the absence of excipient.

The stability of PLASmin™ DNA complexes upon freezing and lyophilization was assessed. Particles were tested with sucrose, trehalose, or no excipient. Particles were tested with and without polyethylene glycol, and with TFA or acetate as the counterion to the polyethylene glycol. DNA stability was assessed by a low (3400×g×1 min) spin to pellet aggregates, and monitoring the absorbance of DNA in the supernatant. See FIG. 11. Stability of the complexes with acetate as the counterion surpassed other formulations in the absence of excipient.

Example 6

The turbidity parameter is defined as the slope of a straight line obtained by plotting log of apparent absorbance of light versus log of incident wavelength of the light. The wavelength used is between about 330 nm and 420 nm. A preparation is identified as colloidally stable if a turbidity parameter of less than −3 is determined. A preparation is identified as colloidally unstable if a turbidity parameter of greater than or equal to −3 is determined.

The turbidity parameter of the compacted nucleic acid particles was assessed before and after lyophilization using various excipients, counterions, and with or without polyethylene glycol. See FIG. 12. Sucrose and trehalose were found to be very effective in maintaining the properties of the pre-lyophilization particles. PEG-acetate similarly was effective in maintaining these properties.

Example 7

Figure 13:
FIG. 13 shows a visualization of particles under the electron microscope. For particles made with CK30-PEG10k acetate in the presence of 0.5 M trehalose, the rod-like compacted particles look identical before and after lyophilization and rehydration.
Figure 13:

Particles were observed under the electron microscope before and after lyophilization. See FIG. 13. Particles made with CK30-PEG10k acetate in the presence of 0.5 M trehalose look similarly rod-like before and after lyophilization and rehydration.

Example 8

Figure 14:
FIG. 14 shows a visualization of particles under the electron microscope. For particles made with CK30 TFA in the presence of 0.5M sucrose, the ellipsoidal particles of compacted DNA look identical before and after lyophilization and rehydration.
Figure 14:
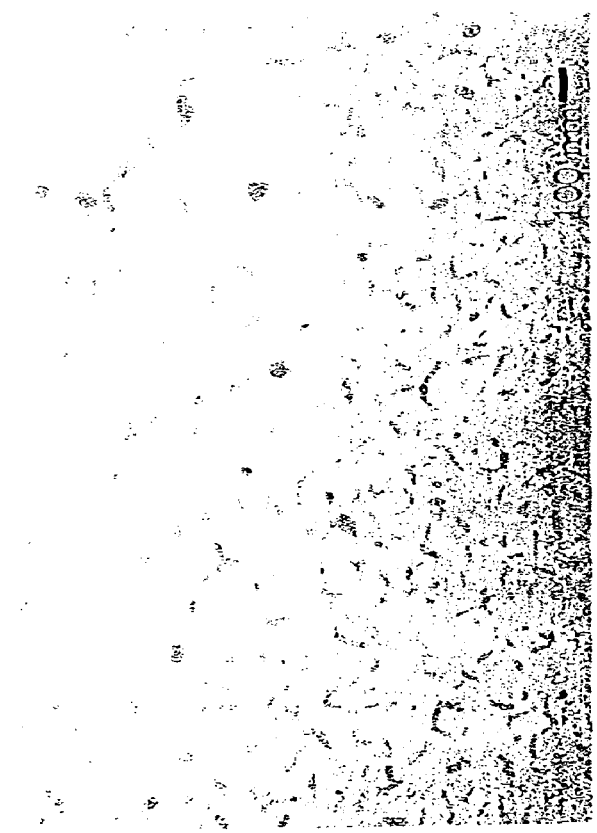

Particles were observed before and after lyophilization and rehydration under the electron microscope. The ellipsoidal particles of compacted DNA made with CK30 TFA (counterion) in the presence of 0.5M sucrose look identical before and after lyophilization and rehydration. See FIG. 14.

Example 9

Figure 15:
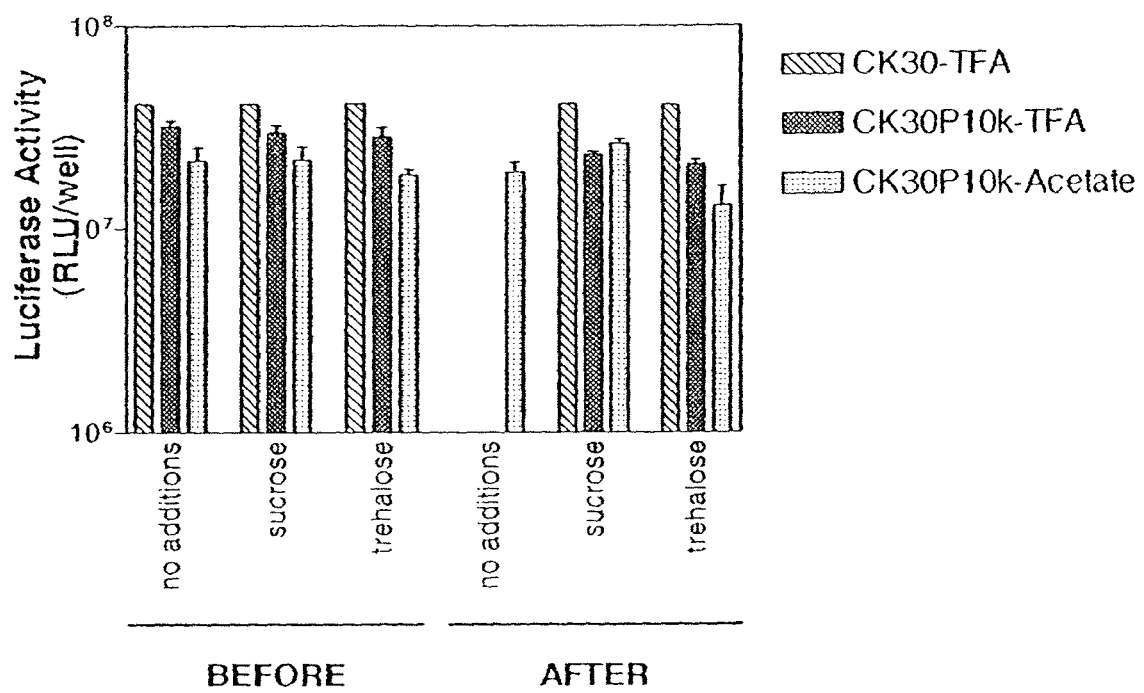
FIG. 15 shows the results of gene transfer experiments using lyophilized PLASmin™ DNA complexes. Luciferase enzyme was encoded by the complexes and its activity was measured as a means of monitoring gene transfer. While sucrose and trehalose were effective in protecting the gene transfer activity to all particles, particles which contained polyethylene glycol (10 kdal) and acetate as a counterion were surprisingly stable to lyophilization, even in the absence of cryoprotectant excipient (disaccharide).

Gene transfer experiments using lyophilized and rehydrated PLASmin™ DNA complexes were performed, comparing them to pre-lyophilization preparations. Luciferase enzyme was encoded by the complexes and its activity was measured as a means of monitoring gene transfer. While sucrose and trehalose were effective in protecting the gene transfer activity to all particles, particles which contained polyethylene glycol (10 kdal) and acetate as a counterion were surprisingly stable to lyophilization, even in the absence of cryoprotectant excipient (disaccharide). See FIG. 15.

Example 10

Polylysines having an N-terminal cysteine and exactly 30 or 45 lysine residues (CK30 or CK45, respectively) were obtained as trifluoroacetate (TFA) salts by solid-phase synthesis. The cysteine residue was then used to conjugate polyethylene glycol (MW 10,000) to form PEG-ylated polylysines CK30P10K and CK45P10K. The TFA counterion was exchanged with acetate, bicarbonate, or chloride by gel filtration. DNA was condensed by these polylysines, dialyzed against 0.9% NaCl, and concentrated to 1 or 4 mg/ml using centrifugal concentrators before analysis. Plasmid DNA having 5921 bp was comprised of kanamycin resistance and luciferase genes, elongation factor-1α promoter and first intron, CMV enhancer, RU5 translational enhancer from HTLV I, SV40 late polyadenylation site, and ColE1 origin of replication was used.

Colloidal stability for the DNA complexes was determined by measuring sedimentation of condensed DNA during centrifugation (3,400 for 1 min) and scattering of light (turbidity) in the wavelength range of 330-415 nm. The turbidity parameter is the slope of a straight line obtained by plotting log of apparent absorbance (due to scattering) vs. log of incident wavelength in a range outside the true absorption by DNA or peptides (330-415 nm). According to the Rayleigh law, particles that are small compared to the wavelength of light should have Turbidity Parameter of −4. Larger particles, however, scatter light differently and have Turbidity Parameters in the range of ~−1 to −3. Very large aggregates, have a Turbidity Parameter of ~−1. We have found that all the tested DNA formulations were colloidally stable in normal saline (0.9% NaCl) as judged by sedimentation and turbidity measurements. We also found that the ability of polylysines to condense DNA depends on type of associated counterions and length of polylysine. CK30P10k with chloride represents the extreme case since it does not condense DNA or condenses it very poorly. (FIG. 16).

Example 11

Figure 18:
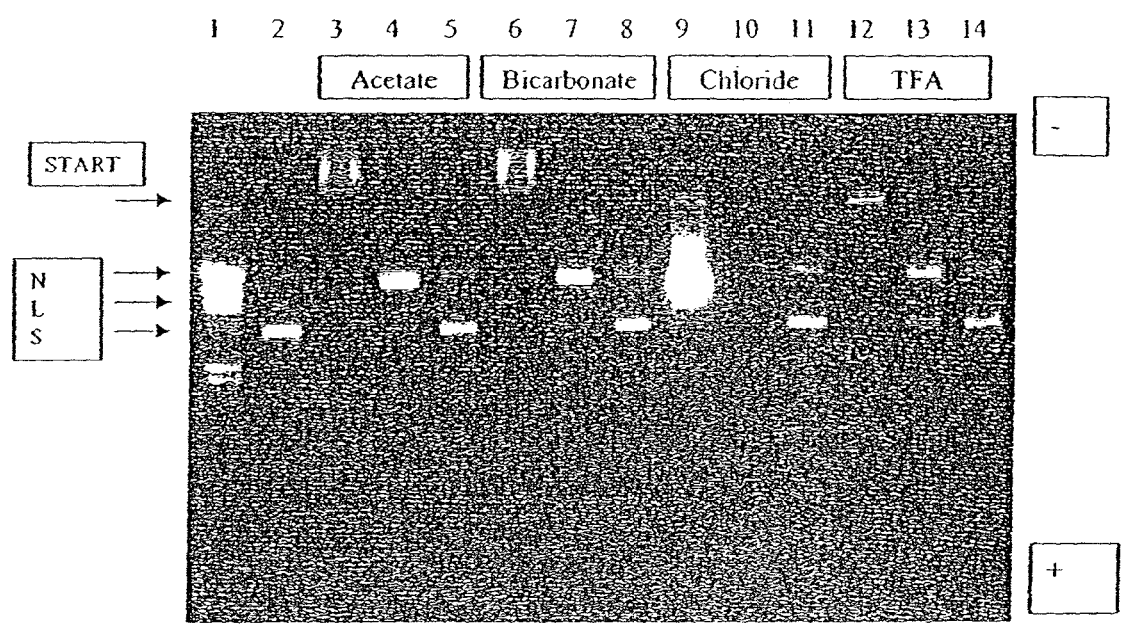
FIG. 18 shows an agarose gel electrophoresis of DNA compacted by PEG-ylated polylysine (CK30P10K) with various counterions. The influence of counterions on the effective net charge of the condensed DNA can be seen by the migration of the compacted DNA through the gel.

DNA compacted by CK30P10K with various counterions was electrophoresed through an agarose gel to examine the effect of counterion on net charge of condensed DNA. DNA samples were loaded directly on the gel (1.5 µg) or after trypsin treatment for 40 min (0.2 µg) to remove polylysine and visualize DNA integrity and relative quantities of supercoiled, nicked, and linear plasmid forms. DNA either migrated to the cathode (CK30/acetate, CK30/bicarbonate, CK45/chloride), remained in the well (CK30/TFA), or migrated to the anode (CK30/chloride). (FIG. 18). Therefore, counterions influence effective net charge of condensed DNA as visualized by gel electrophoresis. Acetate and bicarbonate bound to CK30P10k and chloride bound to CK45P10k result in slightly positive net charge, while TFA results in electrically neutral complexes.

Serum stability was also evaluated for each of the compacted DNA complexes. This was assessed by incubating DNA samples with 75% mouse serum at 37° C. for 2 hr, removing polylysine by trypsinization, and evaluating DNA integrity by gel electrophoresis. Under these conditions, properly condensed DNA is stable, although some nicking and linearization (very little) occurs. Naked DNA, on the other hand, is completely digested within a few minutes (FIG. 18). We found that the ability of polylysines to condense and protect DNA depends on type of associated counterions and length of polylysine. CK30P10k with chloride again represents the extreme case since it does not condense DNA or condenses it very poorly and does not protect against nucleases.

Example 12

Figure 19:
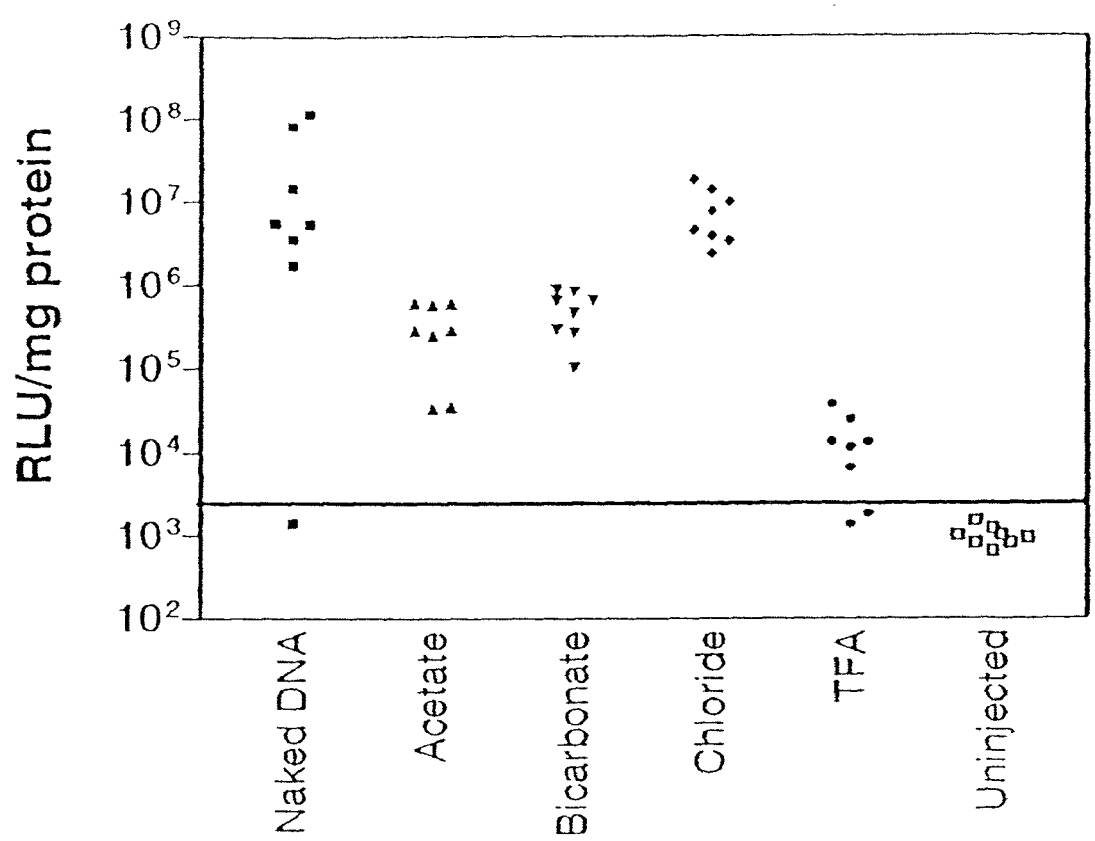
FIG. 19 shows in vivo expression of luciferase plasmid compacted by various counterion forms of PEG-ylated polylysine (CK30P10K) after intramuscular application. Each point represents one animal. The solid line indicates background signal of luciferase assay. Dose was 100 µg DNA.

Intramuscular gene delivery was assessed for each of the counterion forms of CK30P10K. Fifty µl of DNA was injected into quadriceps of each leg of CD-1 mice (4-6 weeks old). The total dose was 100 µg. Prior to the injection, the animals were anesthetized by intraperitoneal injection of a rodent cocktail of Ketamine, Xylazine, and Acepromazine. One day after the injection, the mice were terminated and entire quadrceps removed and processed. Protein and luciferase activity were determined. (FIG. 19).

The morphology of the compacted DNA complexes appears to have influenced their in vivo transfection efficiency. CK30/TFA gave the lowest expression (RLU/mg protein), CK30/acetate and CK30/bicarbonate (more relaxed structures) gave 10-100-fold higher RLU/mg, and CK30/chloride gave the expression at the level of naked DNA (same as or 10-fold higher than CK30/acetate, depending on harvest day). We have found that naked DNA is more efficient than condensed DNA and the TFA formulation is much less efficient than other forms of condensed DNA for intramuscular gene delivery.

Example 13

Figure 20:
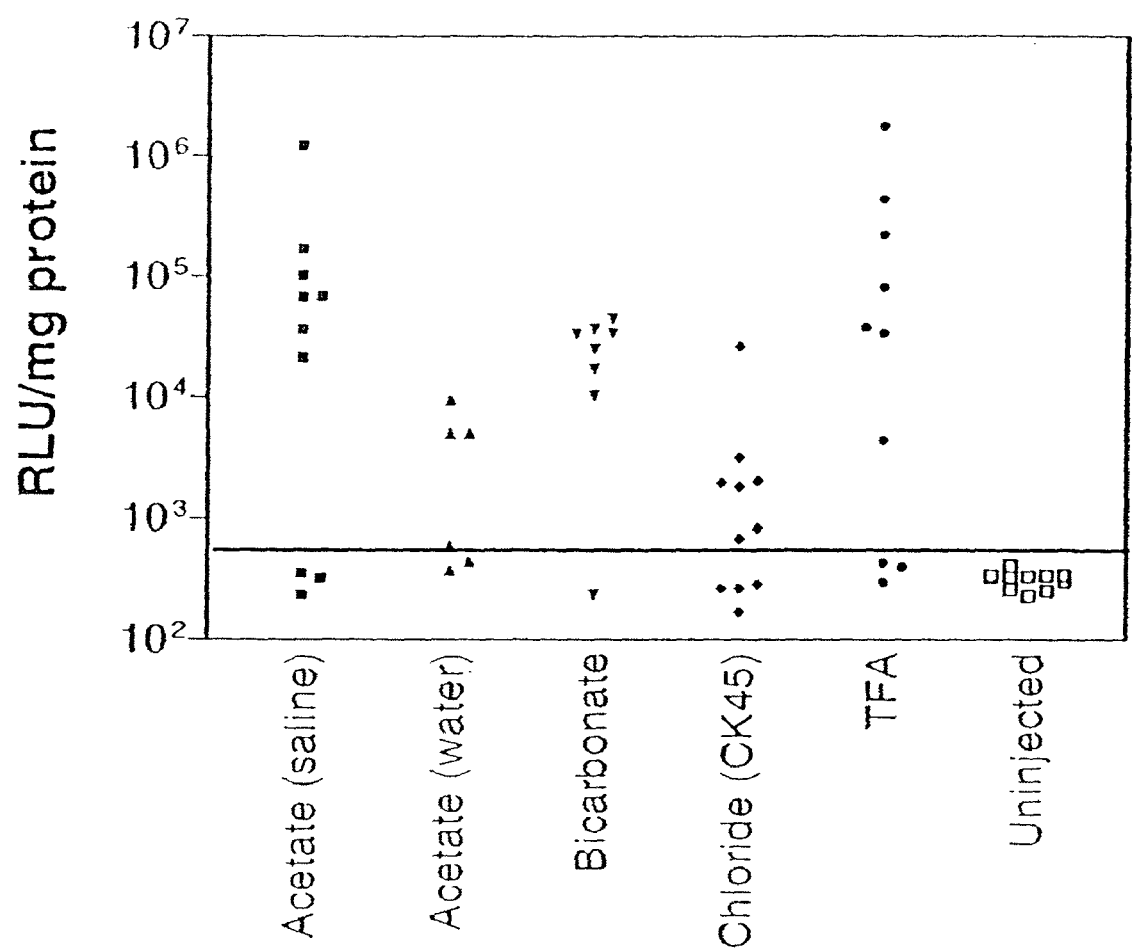
FIG. 20 shows in vivo expression of luciferase plasmid compacted by various forms of PEG-ylated polylysine after intranasal application. Acetate, bicarbonate, and TFA forms of CD30P10K and chloride form of CK45P10K were used. The acetate formulation was prepared either in saline or water. Each point represents one animal. The solid line indicates background signal of luciferase assay. Dose was 100 µg DNA.

Intranasal gene delivery was assessed for each of the counterion forms of CK30P10K. Twenty five µl of DNA was administered in 5-µl aliquots into nostrils of C57/BL6 mice using an automated pipette. The total dose was 100 µg. Prior to the injection, the animals were anesthetized by intraperitoneal injection of a rodent cocktail of Ketamine, Xylazine, and Acepromazine. Two days after the injection, the mice were terminated and entire lungs removed and processed. Protein and luciferase activity were determined (FIG. 20). In intranasal application, the acetate, bicarbonate, and TFA formulations of condensed DNA are the most efficient among the tested formulations, and naked DNA and CK45/chloride were much less effective. We also found that condensed DNA administered intranasally in water is about 10-fold less efficient than the same DNA administered in saline.

LITERATURE CITED

1. Cooper, M. J. (1996) Non-infectious gene transfer and expression systems for cancer gene therapy.
2. Semin. Oncol. 23:172-188 Weiss, R. and Nelson, D. Washington Post, 9/29/99, page A1.
3. Takeshita, S., Gai, D., Leclerc, G., Pickering, J. G., Riesssen, R., Wier, L., and Isner, J. M. (1994) Increased gene expression after liposome-mediated arterial gene transfer associated with intimal smooth muscle cell proliferation. J. Clin. Invest. 93:652-661.
4. Zabner, J., Fasbender, A. J., Moninger, T., Poellinger, D. A., and Welsh, M. J. (1995) Cellular and molecular barriers to gene transfer by a cationic lipid. J. Biol. Chem. 270:18997-19007.
5. Wilke, M., Fortunati, E., van den Broek, M., Hoogeveen, A. T., and Scholte, B. J. (1996) Efficacy of a peptide-based gene delivery system depends on mitotic activity. Gene Ther. 3:1133-1142.
6. Fasbender, A., Zabner, J., Zeiher, B. G., and Welsh, M. J. (1997) A low rate of cell proliferation and reduce DNA uptake limit cationic lipid-mediated gene transfer to primary cultures of ciliated human airway epithelia. Gene Ther. 41173-1180.
7. Sebestyen, M. G., Ludtke, J. J., Bassik, M. C., Zhang, G., Budker, V., Lukhtanov, E. A., Hagstrom, J. E., and Wolff. J. A. (1998) DNA vector chemistry: the covalent attachment of signal peptides to plasmid DNA. Nat. Biotechnol. 16:80-85.
8. Jiang, C., O'Connor, S. P., Fang, S. L., Wang, K. X., Marshall, J., Williams, J. L., Wilburn, B., Echelard, Y., and Cheng, S. (1998) Efficiency of cationic lipid-mediated transfection of polarized and differentiated airway epithelial cells in vitro and in vivo.
9. Tseng, W. C., Haselton, F. R., and Giorgio, T. D. (1999) Mitosis enhances transgene expression of plasmid delivered by cationic liposomes. Biochim. Biophy. Acta 1445: 53-64.
10. Mortimer, J., Tam, P., MacLachlan, I., Graham, R. W., Saravolac, E. G., and Joshi, P. B. (1999) Cationic lipid-mediated transfection of cells in culture requires mitotic activity. Gene Ther. 6:403-411.
11. Mirzayans, R., Aubin, R., and Paterson, M. (1992) Differential expression and stability of foreign genes introduced into human fibroblasts by nuclear versus cytoplasmic microinjection. Mutat. Res. 281:115-122.
12. Dworetzky, S. I. and Feldherr, C. M. (1988) Translocation of RNA-coated gold particles through the nuclear pores of oocytes. J. Cell Biol. 106:575-584.
13. Feldherr, C. M. and Akin D. (1991) Signal-mediated nuclear transport in proliferating and growth-arrested BALB/c 3T3 cells. J. Cell Biol. 115:933-939.

The invention claimed is:

1. A non-naturally occurring composition comprising a plurality of unaggregated nucleic acid complexes, wherein individual complexes of said plurality consist essentially of a single nucleic acid molecule and one or more polycation molecules, wherein said complexes are formed by mixing said nucleic acid molecule and said polycation molecules, wherein prior to mixing said polycation molecules have a counterion selected from the group consisting of acetate, bicarbonate, and chloride, wherein a subset of said complexes are rod-shaped when visualized by transmission electron microscopy, wherein the rod-shaped complexes have a diameter of 10-20 nm when visualized by transmission electron microscopy, wherein the nucleic acid molecules of the rod-shaped complexes are condensed, and wherein said complexes are colloidally stable in normal saline.

2. The composition of claim 1 wherein the polycation molecules are polylysine or a polylysine derivative.

3. The composition of claim 2 wherein the polylysine derivative is polylysine peptide with a cysteine residue.

4. The composition of claim 1, wherein said rod-shaped complexes have a length of 100-300 nm when visualized by transmission electron microscopy.

5. The composition of claim 1, wherein the rod-shaped complexes have a length of 100-200 nm when visualized by transmission electron microscopy.

6. A non-naturally occurring composition comprising a plurality of unaggregated nucleic acid complexes, wherein individual complexes of said plurality consist essentially of a single nucleic acid molecule and one or more polycation molecules, wherein said complexes are formed by mixing said nucleic acid molecule and said polycation molecules, wherein prior to mixing said polycation molecules have a counterion selected from the group consisting of acetate, bicarbonate, and chloride, said polycation molecules having a nucleic acid binding moiety through which they are complexed to the nucleic acid, wherein said nucleic acid molecule encodes at least one functional protein, wherein a subset of said complexes are rod-shaped when visualized by transmission electron microscopy, wherein the rod-shaped complexes have a diameter of 10-20 nm when visualized by transmission electron microscopy, wherein the nucleic acid molecules of the rod-shaped complexes are condensed, and wherein said complexes are colloidally stable in normal saline.

7. The composition of claim 6 wherein the polycation molecules are polylysine or a polylysine derivative.

8. The composition of claim 7 wherein the polylysine derivative is polylysine peptide with a cysteine residue.

9. The non-naturally occurring composition of claim 6 wherein said nucleic acid molecule comprises a promoter which controls transcription of an RNA molecule encoding the functional protein.

10. The non-naturally occurring composition of claim 6 wherein the protein is therapeutic.

11. The non-naturally occurring composition of claim 6 wherein the rod-shaped complexes have a length of 100-300 nm when visualized by transmission electron microscopy.

12. The non-naturally occurring composition of claim 6 wherein the rod-shaped complexes have a length of 100-200 nm when visualized by transmission electron microscopy.

13. A non-naturally occurring composition comprising a plurality of unaggregated nucleic acid complexes, wherein individual complexes of said plurality consist essentially of a single double-stranded cDNA molecule and one or more polycation molecules, wherein said complexes are formed by mixing said nucleic acid molecule and said polycation molecules, wherein prior to mixing said polycation molecules have a counterion selected from the group consisting of acetate, bicarbonate, and chloride, wherein said cDNA molecule encodes at least one functional protein, wherein a subset of said complexes are rod-shaped when visualized by transmission electron microscopy, wherein the nucleic acid molecules of the rod-shaped complexes are condensed, wherein the rod-shaped complexes have a diameter of 10-20 nm when visualized by transmission electron microscopy, and wherein said complexes are colloidally stable in normal saline.

14. The composition of claim 13 wherein the polycation molecules are polylysine or a polylysine derivative.

15. The composition of claim 14 wherein the polylysine derivative is polylysine peptide with a cysteine residue.

16. A non-naturally occurring composition comprising a plurality of soluble compacted complexes of a nucleic acid molecule and one or more polycation molecules, wherein a subset of said complexes are rod-shaped when visualized by transmission electron microscopy, wherein the rod-shaped complexes have a diameter of 10-20 nm when visualized by transmission electron microscopy, wherein individual complexes of said plurality consist essentially of a single nucleic acid molecule and one or more polycation molecules, wherein the nucleic acid molecules of the rod-shaped complexes are condensed, wherein said complexes are colloidally stable in normal saline, wherein said complexes are made by the process of:
    mixing a nucleic acid with a polycation having acetate as a counterion, at a salt concentration sufficient for compaction of the complexes.

17. A non-naturally occurring composition comprising a plurality of soluble compacted complexes of a nucleic acid molecule and one or more polycation molecules, wherein a subset of the complexes are rod-shaped when visualized by transmission electron microscopy, wherein the nucleic acid molecules of the rod-shaped complexes are condensed, wherein the rod-shaped complexes have a diameter of 10-20 nm when visualized by transmission electron microscopy, wherein individual complexes of said plurality consist essentially of a single nucleic acid molecule and one or more polycation molecules wherein said complexes are colloidally stable in normal saline, wherein the complexes are made by the process of:
    mixing a nucleic acid molecule with polycation molecules having acetate as a counterion in a solvent to form a complex, said mixing being performed in the absence of added salt, whereby the nucleic acid forms soluble complexes with the polycation molecules without forming aggregates.

18. The composition of claim 16 wherein the polycation molecules are polylysine or a polylysine derivative.

19. The composition of claim 18 wherein the polylysine derivative is polylysine peptide with a cysteine residue.

20. The composition of claim 17 wherein the polycation molecules are polylysine or a polylysine derivative.

21. The composition of claim 20 wherein the polylysine derivative is polylysine peptide with a cysteine residue.

22. The composition of claim 13 wherein the nucleic acid complexes are associated with a lipid.

23. The composition of claim 13 wherein said rod-shaped complexes have a length of 100-300 nm when visualized by transmission electron microscopy.

24. The composition of claim 13 wherein the rod-shaped complexes have a length of 100-200 nm when visualized by transmission electron microscopy.

25. The composition of claim 1 wherein said polycation molecules are CK15-60P10 and the counterion is acetate, wherein CK15-60P10 is a polyamino acid polymer of one N-terminal cysteine and 15-60 lysine residues, wherein a molecule of polyethylene glycol having an average molecular weight of 10 kdal is attached to the cysteine residue.

26. The composition of claim 25 wherein the polycation molecules comprise 30 residues of lysine.

27. The composition of claim 25 wherein the polycation molecules comprise a targeting moiety.

28. The composition of claim 25, said rod-shaped complexes have a length of 100-300 nm when visualized by transmission electron microscopy.

29. The composition of claim 25, wherein the rod-shaped complexes have a length of 100-200 nm when visualized by transmission electron microscopy.

30. The composition of claim 25 which is lyophilized.

31. The composition of claim 25 which is rehydrated after lyophilization.

32. The composition of claim 25 which does not contain a disaccharide.

33. A method of delivering polynucleotides to cells comprising:
    contacting the composition of claim 31 with cells, whereby the nucleic acid is delivered to and taken up by the cells.

34. The method of claim 33 wherein the composition does not contain a disaccharide.

35. The composition of claim 6 wherein the polycation molecules are CK15-60P10, and the counterion is acetate, wherein CK15-60 is a polyamino acid polymer of one N-terminal cysteine and 15-60 lysine residues, wherein a molecule of polyethylene glycol having an average molecular weight of 10 kdal is attached to the cysteine residue.

36. The composition of claim 35 wherein the polycation molecules comprise 30 residues of lysine.

37. The composition of claim 35 wherein the polycation molecules comprise a targeting moiety.

38. The composition of claim 35 which is lyophilized.

39. The non-naturally occurring composition of claim 35 wherein said nucleic acid molecule comprises a promoter which controls transcription of an RNA molecule encoding the functional protein.

40. The non-naturally occurring composition of claim 35 wherein the protein is therapeutic.

41. The non-naturally occurring composition of claim 35 wherein the rod-shaped complexes have a length of 100-300 nm when visualized by transmission electron microscopy.

42. The non-naturally occurring composition of claim 35 wherein the rod-shaped complexes have a length of 100-200 nm when visualized by transmission electron microscopy.

43. The composition of claim 35 which is rehydrated after lyophilization.

44. The composition of claim 35 which does not contain a disaccharide.

45. A method of delivering polynucleotides to cells comprising:
contacting the composition of claim 43 with cells, wherein the polynucleotide encodes a protein, whereby the protein is expressed.

46. The composition of claim 13 wherein said polycation molecules are CK15-60P10, and said counterion is acetate, wherein CK15-60P10 is a polyamino acid polymer of one N-terminal cysteine and 15-60 lysine residues, wherein a molecule of polyethylene glycol having an average molecular weight of 10 kdal is attached to the cysteine residue.

47. The composition of claim 46 wherein the polycation molecules comprise 30 residues of lysine.

48. The composition of claim 46 wherein the polycation molecules comprise a targeting moiety.

49. The composition of claim 46 which is lyophilized.

50. The composition of claim 46 which is rehydrated after lyophilization.

51. The composition of claim 46 which does not contain a disaccharide.

52. A method of delivering polynucleotides to cells comprising:
contacting the composition of claim 50 with cells, wherein the polynucleotide encodes a protein, whereby the protein is expressed.

53. The composition of claim 6 wherein the nucleic acid complexes are associated with a lipid.

54. The composition of claim 13 wherein the nucleic acid complexes are associated with a lipid.

55. The composition of claim 16 wherein the complexes have a length of 100-300 nm.

56. The composition of claim 16 wherein the complexes have a length of 100-200 nm.

57. The composition of claim 17 wherein the complexes have a length of 100-300 nm.

58. The composition of claim 17 wherein the complexes have a length of 100-200 nm.

59. The method of claim 45 wherein the composition does not contain a disaccharide.

* * * * *